US012662497B2

(12) United States Patent
Zhu et al.

(10) Patent No.: US 12,662,497 B2
(45) Date of Patent: Jun. 23, 2026

(54) BENZAZEPINE COMPOUNDS, PREPARATION METHOD THEREFOR AND PHARMACEUTICAL USE THEREOF

(71) Applicants: Shanghai Senhui Medicine Co., Ltd., Shanghai (CN); Shanghai Shengdi Pharmaceutical Co., Ltd., Shanghai (CN); Jiangsu Hengrui Pharmaceuticals Co., Ltd., Lianyungang (CN)

(72) Inventors: Lingjian Zhu, Shanghai (CN); Jianyu Shi, Shanghai (CN); Changjin Ji, Shanghai (CN); Bangjie Dong, Shanghai (CN); Jian Huang, Shanghai (CN)

(73) Assignees: Shanghai Senhui Medicine Co., Ltd., Shanghai (CN); Shanghai Shengdi Pharmaceutical Co., Ltd., Shanghai (CN); Jiangsu Hengrui Pharmaceuticals Co., Ltd., Jiangsu (CN)

( * ) Notice: Subject to any disclaimer, the term of this patent is extended or adjusted under 35 U.S.C. 154(b) by 419 days.

(21) Appl. No.: 18/264,986

(22) PCT Filed: Feb. 10, 2022

(86) PCT No.: PCT/CN2022/075793
§ 371 (c)(1),
(2) Date: Aug. 10, 2023

(87) PCT Pub. No.: WO2022/171160
PCT Pub. Date: Aug. 18, 2022

(65) Prior Publication Data

US 2024/0309030 A1 Sep. 19, 2024

(30) Foreign Application Priority Data

Feb. 10, 2021 (CN) ......................... 202110184339.1
Jul. 16, 2021 (CN) ......................... 202110803896.7
(Continued)

(51) Int. Cl.
*C07D 223/16* (2006.01)
*A61K 31/55* (2006.01)
(Continued)

(52) U.S. Cl.
CPC ............ *C07F 9/5535* (2013.01); *A61K 31/55* (2013.01); *A61K 31/675* (2013.01); *C07D 223/16* (2013.01)

(58) Field of Classification Search
CPC ..... C07D 223/16; C07F 9/5535; A61K 31/55; A61K 31/675
See application file for complete search history.

(56) References Cited

U.S. PATENT DOCUMENTS 5,258,510 A 11/1993 Ogawa et al.
8,785,386 B2 * 7/2014 Kondo ...................... A61P 9/08
514/15.6

FOREIGN PATENT DOCUMENTS

CN 101346390 A 1/2009
CN 102030709 A 4/2011
(Continued)

OTHER PUBLICATIONS

International Search Report issued May 7, 2022 in PCT/CN2022/075793.
Written Opinion issued May 7, 2022 in PCT/CN2022/075793.

*Primary Examiner* — D Margaret M Seaman
(74) *Attorney, Agent, or Firm* — ICE MILLER LLP

(57) ABSTRACT

Benzazepine compounds, a preparation method therefor and pharmaceutical use thereof. Specifically, the present invention relates to a compound represented by formula II-1 or formula VIII-1, a pharmaceutical composition containing same, and pharmaceutical use thereof. The benzazepine compounds can be used for treating diseases associated with vasopressin receptors, in particular hypertension, heart disease, etc.

II-1

(Continued)

-continued

VIII-1

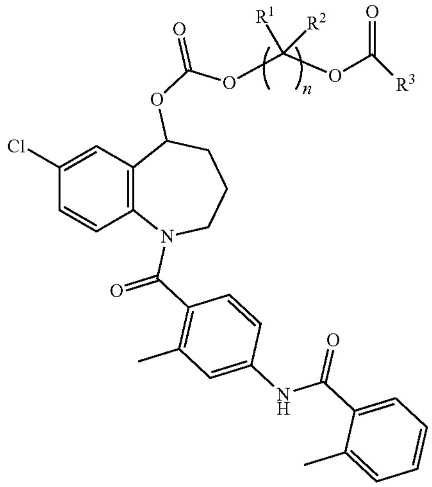

19 Claims, 1 Drawing Sheet

(30) Foreign Application Priority Data

| | | |
|---|---|---|
| Jul. 26, 2021 | (CN) | 202110846383.4 |
| Nov. 16, 2021 | (CN) | 202111356862.4 |
| Nov. 24, 2021 | (CN) | 202111407094.0 |

(51) Int. Cl.

| | |
|---|---|
| ***A61K 31/675*** | (2006.01) |
| ***C07F 9/553*** | (2006.01) |

(56) References Cited

FOREIGN PATENT DOCUMENTS

| | | | |
|---|---|---|---|
| CN | 103342679 A | | 10/2013 |
| JP | 2009-29793 | * | 2/2009 |

* cited by examiner

BENZAZEPINE COMPOUNDS, PREPARATION METHOD THEREFOR AND PHARMACEUTICAL USE THEREOF

CROSS-REFERENCE TO RELATED APPLICATION

This application is a Section 371 of International Application No. PCT/CN2022/075793 filed Feb. 10, 2022, which was published in the Chinese language Aug. 18, 2022, under International Publication No. WO 2022/171160 A1, which claims priority to Chinese Patent Application No. 202110184339.1 filed Feb. 10, 2021, Chinese Patent Application No. 202110803896.7 filed Jul. 16, 2021, Chinese Patent Application No. 202110846383.4 filed Jul. 26, 2021, Chinese Patent Application No. 202111356862.4 filed Nov. 16, 2021, and Chinese Patent Application No. 202111407094.0 filed Nov. 24, 2021, the disclosures of which are incorporated herein by reference in their entireties.

TECHNICAL FIELD

The present disclosure belongs to the field of pharmaceutics, and relates to a benzazepine compound, a preparation method therefor, a composition thereof and pharmaceutical use thereof.

BACKGROUND

Vasopressin is a nonapeptide hormone secreted primarily by the posterior pituitary gland, which acts via the vascular $V_1$ receptor and renal $V_2$ receptor subtypes. The $V_2$ receptor present in the kidney can stimulate adenylate cyclase to achieve the effect of arresting urine production. Vasopressin receptor antagonists have very wide applications. It can be used for treating diseases such as hypertension, congestive heart failure, cirrhosis, renal failure and cerebral edema. Benzazepines are small-molecule vasopressin $V_2$ receptor antagonists. Tolvaptan is the first commercially available compound of this kind. Tolvaptan blocks the binding of vasopressin to the collecting duct $V_2$ receptor, preventing aquaporin-2 from moving to the cell membrane surface, inhibiting urine concentration, and increasing free water excretion without sodium excretion, thereby achieving the diuretic effect (J Clin Med, 2014, 3(4): 1276-1290). In animal experiments, tolvaptan showed the diuretic effect in both rats and dogs and, compared to furosemide, it significantly increased the elimination of electrolytes and water and increased the concentration of sodium ions (Circulation, 2003, 107, 690-2696). In two other clinical trials carried out in patients with hyponatremia caused by congestive heart failure (CHF) and cirrhosis, the compound was well tolerated and could rapidly and effectively elevate the concentration of sodium ions in serum without producing side effects such as dry mouth and thirst and without having to restrict water intake. It applies to clinically significant high-volume hyponatremia and normal-volume hyponatremia, including those combined with heart failure, cirrhosis and syndrome of inappropriate antidiuretic hormone secretion (SIADH) (Chinese Journal of New Drugs, 2010, 19(10): 819-822).

Tolvaptan is a known compound. It has been disclosed in the U.S. Pat. No. 5,258,510. Its structure is shown below:

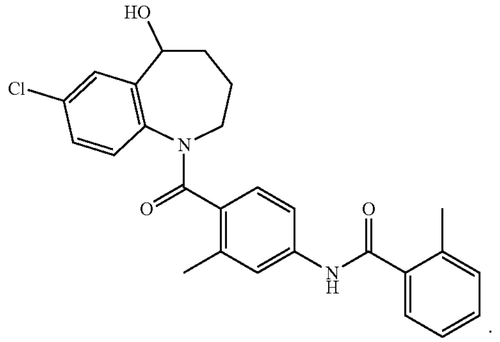 [SMILES: Cc1ccccc1C(=O)Nc1ccc(C(=O)N2CCCC(O)c3cc(Cl)ccc32)c(C)c1]

However, its administration is limited due to its low solubility in water, insufficient intestinal absorption, and the like. WO2009001968A discloses a benzazepine derivative useful as a vasopressin antagonist and studied derivatives of tolvaptan. In addition, CN101346390A discloses a novel phosphate derivative of tolvaptan, which is useful for improving its solubility in water.

SUMMARY

One aspect of the present disclosure provides a compound of formula I-1 or a pharmaceutically acceptable salt thereof,

I-1

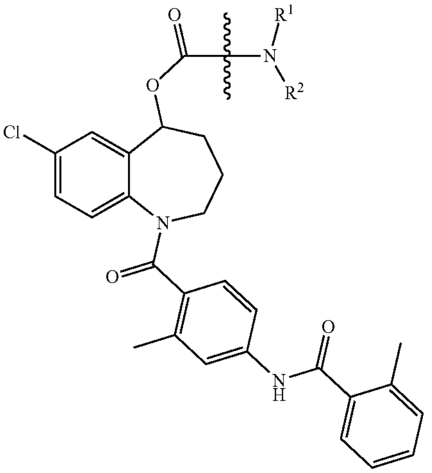

wherein:

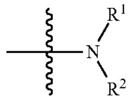

is an amino acid residue; or

- $R^1$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with A;
- $R^2$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with A;

or $R^1$ and $R^2$, together with the N atom to which they are attached, form a 3-12 membered heterocyclyl group containing 1-3 heteroatoms; the 3-12 membered heterocyclyl group is optionally further substituted with A;

A is selected from the group consisting of H, —COOH, —$NH_2$, —OH, halogen, cyano, nitro, oxo, $C_{1-6}$ alkyl, $C_{3-8}$ cycloalkyl and 3-12 membered heterocyclyl; the —$NH_2$, $C_{1-6}$ alkyl, $C_{3-8}$ cycloalkyl and 3-12 membered heterocyclyl are optionally substituted with $R^4$;

$R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure,

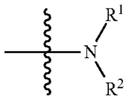

is an amino acid residue; the amino acid is selected from the group consisting of alanine, arginine, aspartic acid, cysteine, glutamine, glutamic acid, histidine, isoleucine, glycine, leucine, lysine, methionine, phenylalanine, serine, threonine, tyrosine and valine.

In an alternative embodiment, in the compound of formula I-1 or the pharmaceutically acceptable salt thereof provided in the present disclosure,

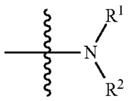

is an amino acid residue; the amino acid residue is glutamic acid.

In an alternative embodiment, in the compound of formula I-1 or the pharmaceutically acceptable salt thereof provided in the present disclosure, $R^1$ and $R^2$, together with the N atom to which they are attached, form a 3-8 membered heterocyclyl group containing 1-3 heteroatoms; the 3-8 membered heterocyclyl group is optionally substituted with A; A is selected from the group consisting of H, —COOH, —$NH_2$, —OH, halogen, cyano, nitro, oxo, $C_{1-6}$ alkyl, $C_{3-8}$ cycloalkyl and 3-12 membered heterocyclyl; the —$NH_2$, $C_{1-6}$ alkyl, $C_{3-8}$ cycloalkyl and 3-12 membered heterocyclyl are optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl. In an alternative embodiment, in the compound of formula I-1 or the pharmaceutically acceptable salt thereof provided in the present disclosure, $R^1$ and $R^2$, together with the N atom to which they are attached, form a 3-8 membered heterocyclyl group containing 1 heteroatom.

In an alternative embodiment, in the compound of formula I-1 or the pharmaceutically acceptable salt thereof provided in the present disclosure, A is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, A is selected from 3-12 membered heterocyclyl, and the 3-12 membered heterocyclyl is optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, A is selected from 3-8 membered heterocyclyl, and the 3-8 membered heterocyclyl is optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, A is selected from 5-6 membered heterocyclyl, wherein the atom of attachment of A is a heteroatom, and the heteroatom is selected from N; the 5-6 membered heterocyclyl is optionally substituted with $R^4$, and $R^4$ is selected from the group consisting of halogen, —OH, $C_{1-6}$ alkyl and $C_{1-6}$ alkoxy.

In an alternative embodiment, in the compound of formula I-1 or the pharmaceutically acceptable salt thereof provided in the present disclosure, A is selected from 5-6 membered heterocyclyl, wherein the atom of attachment of A is a heteroatom, and the heteroatom is selected from N.

In an alternative embodiment, in the compound of formula I-1 or the pharmaceutically acceptable salt thereof provided in the present disclosure, $R^1$ is selected from $C_{1-6}$ alkyl, and the $C_{1-6}$ alkyl is optionally substituted with A; $R^2$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with A; A is selected from the group consisting of H, —COOH, —$NH_2$, —OH, halogen, cyano, nitro, oxo, $C_{1-6}$ alkyl, $C_{3-8}$ cycloalkyl and 3-12 membered heterocyclyl; the —$NH_2$, $C_{1-6}$ alkyl, $C_{3-8}$ cycloalkyl and 3-12 membered heterocyclyl are optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, $R^1$ is selected from $C_{1-6}$ alkyl, and the $C_{1-6}$ alkyl is optionally substituted with A; $R^2$ is selected from $C_{1-6}$ alkyl, and the $C_{1-6}$ alkyl is optionally substituted with A; A is selected from the group consisting of H, —COOH, —$NH_2$, —OH, halogen, cyano, nitro, oxo, $C_{1-6}$ alkyl, $C_{3-8}$ cycloalkyl and 3-12 membered heterocyclyl; the —$NH_2$, $C_{1-6}$ alkyl, $C_{3-8}$ cycloalkyl and 3-12 membered heterocyclyl are optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, $R^1$ is selected from $C_{1-6}$ alkyl, and the $C_{1-6}$ alkyl is optionally substituted with A; $R^2$ is selected from $C_{1-6}$ alkyl, and the $C_{1-6}$ alkyl is optionally substituted with A; A is selected from the group consisting of H, —COOH, —$NH_2$, —OH, halogen, $C_{1-6}$ alkyl, $C_{3-8}$ cycloalkyl and 3-12 membered heterocyclyl; the —$NH_2$, $C_{1-6}$ alkyl, $C_{3-8}$ cycloalkyl and 3-12 membered heterocyclyl are optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, $R^1$ is selected from $C_{1-6}$ alkyl, and the $C_{1-6}$ alkyl is optionally substituted with A; $R^2$ is selected from $C_{1-6}$ alkyl, and the $C_{1-6}$ alkyl is optionally substituted with A; A is selected from the group consisting of H, $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with $R^4$; $R^4$ is selected from the group consisting of halogen, —$NH_2$, —OH, $C_{1-6}$ alkyl, $C_{1-6}$ alkoxy and $C_{3-8}$ cycloalkyl.

In an alternative embodiment, in the compound of formula I-1 or the pharmaceutically acceptable salt thereof provided in the present disclosure, $R^1$ is selected from $C_{1-6}$ alkyl, and the $C_{1-6}$ alkyl is optionally substituted with A; $R^2$ is selected from the group consisting of $C_{1-6}$ alkyl, and the $C_{1-6}$ alkyl is optionally substituted with A; the A is selected from the group consisting of H and 3-12 membered heterocyclyl; preferably, A is 3-8 membered heterocyclyl; more preferably, A is 5-7 membered heterocyclyl.

In an alternative embodiment, in the compound of formula I-1 or the pharmaceutically acceptable salt thereof provided in the present disclosure, $R^1$ is selected from $C_{1-6}$ alkyl; $R^2$ is selected from $C_{1-6}$ alkyl, and the $C_{1-6}$ alkyl is substituted with A; the A is selected from the group consisting of H and 3-12 membered heterocyclyl; preferably, A is 3-8 membered heterocyclyl; more preferably, A is 5-7 membered heterocyclyl.

In an alternative embodiment, in the compound of formula I-1 or the pharmaceutically acceptable salt thereof provided in the present disclosure, $R^1$ is selected from $C_{1-3}$ alkyl; $R^2$ is selected from $C_{1-3}$ alkyl, and the $C_{1-3}$ alkyl is substituted with A; the A is selected from the group consisting of H and 3-12 membered heterocyclyl; preferably, A is 3-8 membered heterocyclyl; more preferably, A is 5-7 membered heterocyclyl.

In an alternative embodiment, in the compound of formula I-1 or the pharmaceutically acceptable salt thereof provided in the present disclosure, $R^1$ is selected from $C_{1-3}$ alkyl; $R^2$ is selected from $C_{1-3}$ alkyl, and the $C_{1-3}$ alkyl is substituted with A; the A is selected from the group consisting of H and 5-7 membered heterocyclyl.

In an alternative embodiment, in the compound of formula I-1 or the pharmaceutically acceptable salt thereof provided in the present disclosure, the compound of formula I-1 is selected from the group consisting of:

1-e

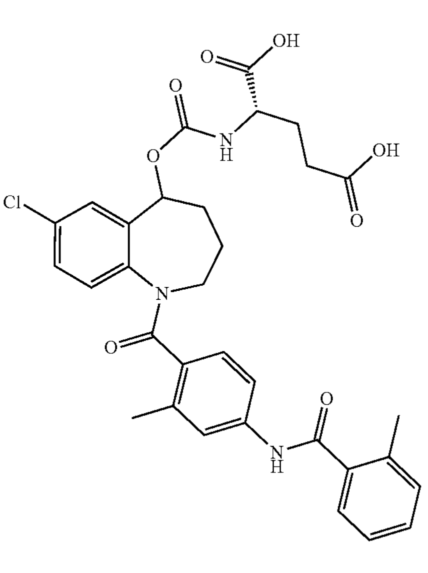

-continued

1

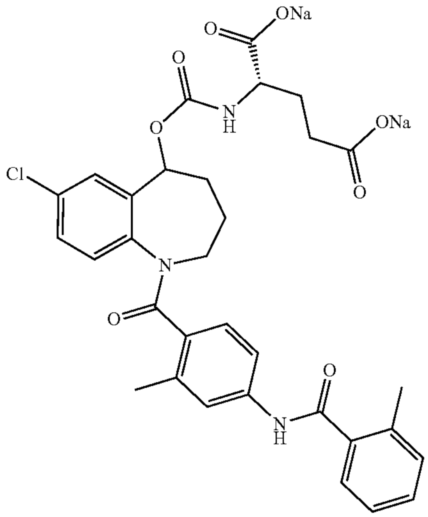

2

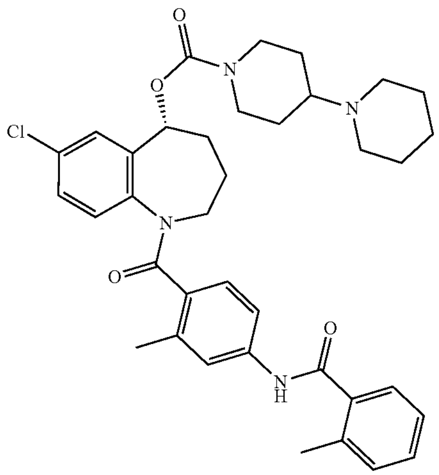

and

3

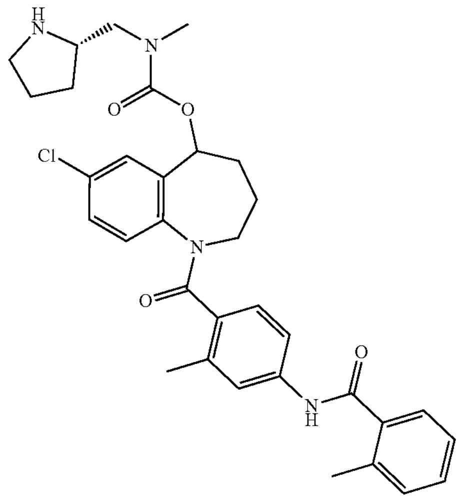

.

Another aspect of the present disclosure provides a compound of formula II-1 or a pharmaceutically acceptable salt thereof,

II-1

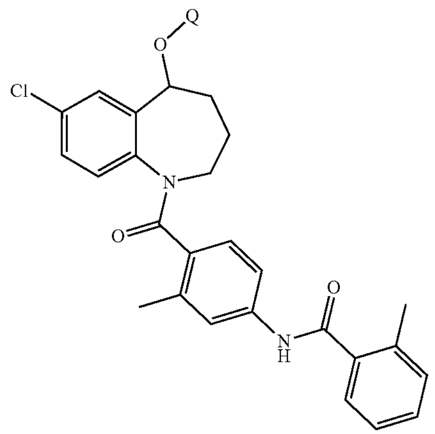

Q is

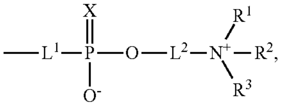

wherein:

$L^1$ is $-(CH_2)_m-$, and the $-(CH_2)-$ is optionally replaced by a heteroatom selected from the group consisting of O, S and N;

$L^2$ is $-(CH_2)_n-$, and the $-(CH_2)-$ is optionally replaced by a heteroatom selected from the group consisting of O, S and N;

m is selected from the group consisting of 0, 1, 2, 3, 4, 5 and 6;

n is selected from the group consisting of 1, 2, 3, 4, 5 and 6;

the $-(CH_2)-$ of $L^2$ is optionally substituted with A;

X is selected from the group consisting of O and S;

$R^1$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with group B;

$R^2$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with group B;

$R^3$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with group B;

or $R^1$ and $R^2$ or $R^2$ and $R^3$, together with the N atom to which they are attached, form a 3-12 membered heterocyclyl group containing 1-3 heteroatoms; the 3-12 membered heterocyclyl group is optionally substituted with group B;

A is selected from the group consisting of H, $-COOH$, $-NH_2$, $-OH$, halogen, cyano, nitro, oxo, $C_{1-6}$ alkyl, $C_{1-6}$ alkoxy, $C_{3-8}$ cycloalkyl, 3-12 membered heterocyclyl, $-COR^4$, $-NHCOR^4$ and $-OCOR^4$; the $-NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, $-NH_2$, $-OH$, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of $-COOH$, $-NH_2$, $-OH$, halogen, cyano, nitro, oxo, $C_{1-6}$ alkyl and $C_{1-6}$ alkoxy;

group B is selected from the group consisting of H, $-COOH$, $-NH_2$, $-OH$, halogen, cyano, nitro and oxo.

In an alternative embodiment, in the compound of formula II-1 or the pharmaceutically acceptable salt thereof provided in the present disclosure, X is O.

In an alternative embodiment, in the compound of formula II-1 or the pharmaceutically acceptable salt thereof provided in the present disclosure, m is selected from the group consisting of 0, 1, 2, 3, 4 and 5.

In an alternative embodiment, in the compound of formula II-1 or the pharmaceutically acceptable salt thereof provided in the present disclosure, m is selected from the group consisting of 0, 1, 2 and 3.

In an alternative embodiment, in the compound of formula II-1 or the pharmaceutically acceptable salt thereof provided in the present disclosure, n is selected from the group consisting of 2, 3, 4 and 5.

In an alternative embodiment, in the compound of formula II-1 or the pharmaceutically acceptable salt thereof provided in the present disclosure, n is selected from the group consisting of 2 and 3.

In an alternative embodiment, in the compound of formula II-1 or the pharmaceutically acceptable salt thereof provided in the present disclosure, A is selected from the group consisting of H, $-COOH$, $-NH_2$, $-OH$, halogen, cyano, nitro, oxo, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with $R^4$; $R^4$ is selected from the group consisting of halogen, $-NH_2$, $-OH$ and $C_{1-6}$ alkyl.

In an alternative embodiment, in the compound of formula II-1 or the pharmaceutically acceptable salt thereof provided in the present disclosure, A is selected from the group consisting of H, $-COOH$, $-NH_2$, $-OH$, halogen, cyano and nitro.

In an alternative embodiment, in the compound of formula II-1 or the pharmaceutically acceptable salt thereof provided in the present disclosure, the $-(CH_2)-$ is unsubstituted.

In an alternative embodiment, in the compound of formula II-1 or the pharmaceutically acceptable salt thereof provided in the present disclosure, $L^1$ is $-CH_2-O-$.

In an alternative embodiment, in the compound of formula II-1 or the pharmaceutically acceptable salt thereof provided in the present disclosure, $L^1$ is $-(CH_2)_m-$, and m is 0.

In an alternative embodiment, in the compound of formula II-1 or the pharmaceutically acceptable salt thereof provided in the present disclosure, $L^2$ is $-(CH_2)_2-$.

In an alternative embodiment, in the compound of formula II-1 or the pharmaceutically acceptable salt thereof provided in the present disclosure, $R^1$ is selected from $C_{1-6}$ alkyl.

In an alternative embodiment, in the compound of formula II-1 or the pharmaceutically acceptable salt thereof provided in the present disclosure, $R^1$ is selected from $C_{1-3}$ alkyl.

In an alternative embodiment, in the compound of formula II-1 or the pharmaceutically acceptable salt thereof provided in the present disclosure, $R^2$ is selected from $C_{1-6}$ alkyl.

In an alternative embodiment, in the compound of formula II-1 or the pharmaceutically acceptable salt thereof provided in the present disclosure, $R^2$ is selected from $C_{1-3}$ alkyl.

In an alternative embodiment, in the compound of formula II-1 or the pharmaceutically acceptable salt thereof provided in the present disclosure, $R^3$ is selected from $C_{1-6}$ alkyl.

In an alternative embodiment, in the compound of formula II-1 or the pharmaceutically acceptable salt thereof provided in the present disclosure, $R^3$ is selected from $C_{1-3}$ alkyl.

In an alternative embodiment, in the compound of formula II-1 or the pharmaceutically acceptable salt thereof provided in the present disclosure, $R^1$ is selected from $C_{1-6}$ alkyl;

$R^2$ is selected from $C_{1-6}$ alkyl;

$R^3$ is selected from $C_{1-6}$ alkyl;

the $C_{1-6}$ alkyl is optionally substituted with group B; group B is selected from the group consisting of H, —COOH, —$NH_2$, —OH, halogen, cyano, nitro and oxo.

In an alternative embodiment, in the compound of formula II-1 or the pharmaceutically acceptable salt thereof provided in the present disclosure, X is O;

$L^1$ is —$(CH_2)_m$—, and m is 0; or $L^1$ is —$CH_2$—O—;

$L^2$ is —$(CH_2)_n$—; n is selected from the group consisting of 2 and 3;

$R^1$ is selected from the group consisting of methyl, ethyl, n-propyl and isopropyl;

$R^2$ is selected from the group consisting of methyl, ethyl, n-propyl and isopropyl;

$R^3$ is selected from the group consisting of methyl, ethyl, n-propyl and isopropyl.

In an alternative embodiment, in the compound of formula II-1 or the pharmaceutically acceptable salt thereof provided in the present disclosure, X is O;

$L^1$ is —$(CH_2)_m$—, and m is 0; or $L^1$ is —$CH_2$—O—;

$L^2$ is —$(CH_2)_n$—; n is selected from the group consisting of 2 and 3;

$R^1$ is selected from methyl; $R^2$ is selected from methyl; $R^3$ is selected from methyl.

In an alternative embodiment, in the compound of formula II-1 or the pharmaceutically acceptable salt thereof provided in the present disclosure, the compound is selected from the group consisting of:

4

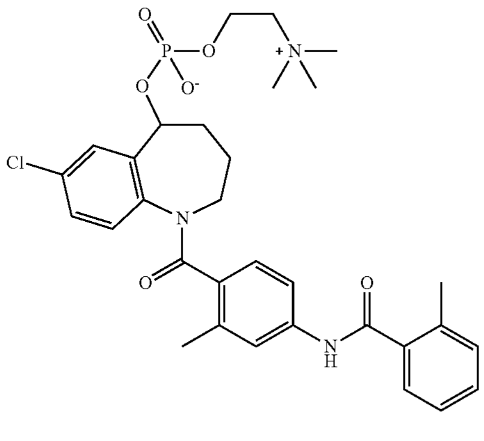

and

-continued

5

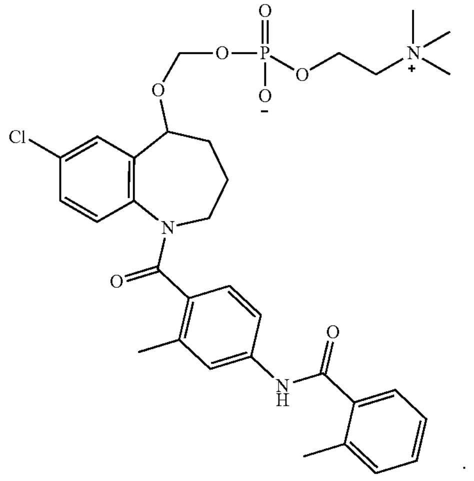

Another aspect of the present disclosure provides a compound of formula III-1 or a pharmaceutically acceptable salt thereof,

III-1

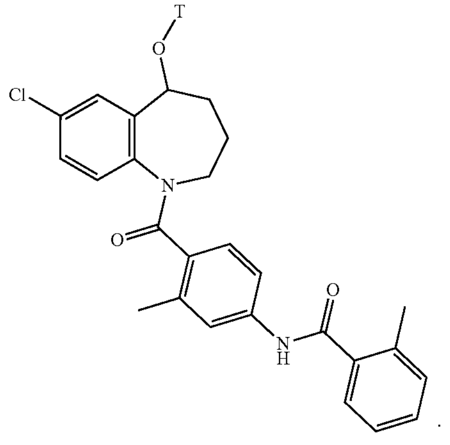

wherein,

T is an amino acid residue, wherein the carboxyl group of the amino acid is attached to O; the amino acid is not glycine or valine.

In the compound of formula III-1 or the pharmaceutically acceptable salt thereof provided in the present disclosure, the amino acid is selected from the group consisting of alanine, arginine, aspartic acid, cysteine, glutamine, glutamic acid, histidine, isoleucine, glycine, leucine, lysine, methionine, phenylalanine, serine, threonine, tyrosine and valine.

In an alternative embodiment, in the compound of formula III-1 or the pharmaceutically acceptable salt thereof provided in the present disclosure, T is an -amino acid residue, wherein the carboxyl group of the amino acid is attached to 0, and the amino acid is glutamic acid, proline or lysine.

In an alternative embodiment, in the compound of formula III-1 or the pharmaceutically acceptable salt thereof provided in the present disclosure, the compound of formula III-1 is selected from the group consisting of

6

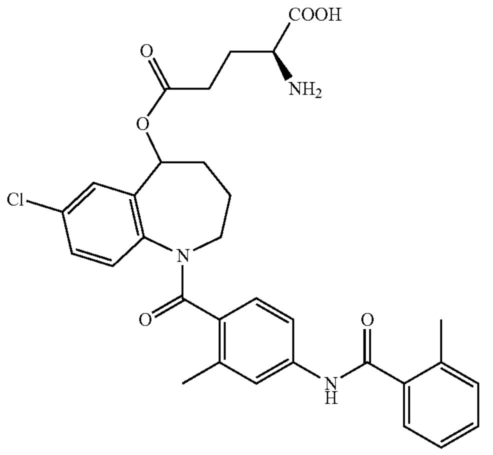

7

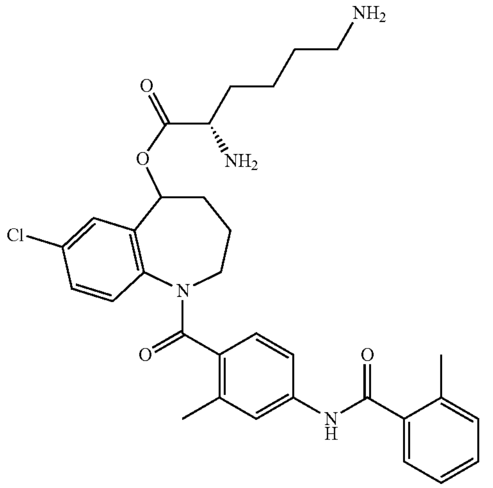

8

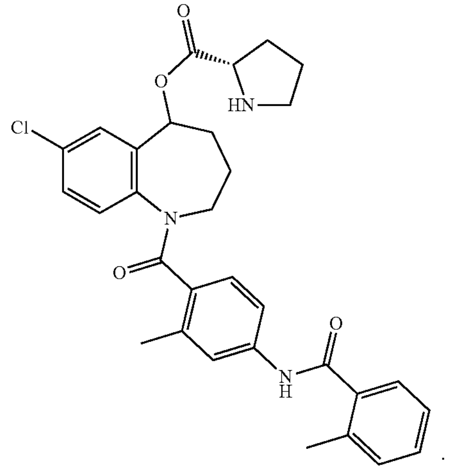

Another aspect of the present disclosure provides a compound of formula IV-1 or a pharmaceutically acceptable salt thereof,

IV-1

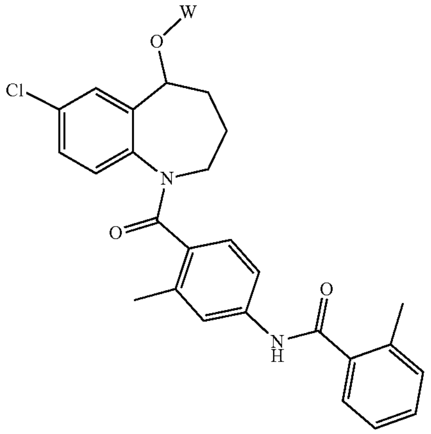

wherein,

W is —C(O)-L-NR$^1$R$^2$R$^3$, wherein:

L is —(CH$_2$)$_n$—, and n is selected from the group consisting of 1, 2, 3, 4, 5 and 6; the —(CH$_2$)— is optionally substituted with A;

R$^1$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally further substituted with group B;

R$^2$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally further substituted with group B;

R$^3$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally further substituted with group B;

or R$^1$ and R$^2$ or R$^2$ and R$^3$, together with the N atom to which they are attached, form a 3-12 membered heterocyclyl group containing 1-3 heteroatoms; the 3-12 membered heterocyclyl group is optionally further substituted with group B;

A is selected from the group consisting of H, —COOH, —NH$_2$, —OH, halogen, cyano, nitro, oxo, $C_{1-6}$ alkyl, $C_{1-6}$ alkoxy, $C_{3-8}$ cycloalkyl, 3-12 membered heterocyclyl, —COR$^4$, —NHCOR$^4$ and —OCOR$^4$; the —NH$_2$, $C_{1-6}$ alkyl, $C_{1-6}$ alkoxy, $C_{3-8}$ cycloalkyl and 3-12 membered heterocyclyl are optionally substituted with R$^4$;

R$^4$ is selected from the group consisting of halogen, —NH$_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally further substituted with one or more groups selected from the group consisting of —COOH, —NH$_2$, —OH, halogen, cyano, nitro, oxo, $C_{1-6}$ alkyl and $C_{1-6}$ alkoxy;

group B is selected from the group consisting of H, —COOH, —NH$_2$, —OH, halogen, cyano, nitro and oxo.

In an alternative embodiment, in the compound of formula IV-1 or the pharmaceutically acceptable salt thereof provided in the present disclosure, n is selected from the group consisting of 2, 3, 4 and 5.

In an alternative embodiment, in the compound of formula IV-1 or the pharmaceutically acceptable salt thereof provided in the present disclosure, n is selected from the group consisting of 2 and 3.

In an alternative embodiment, in the compound of formula IV-1 or the pharmaceutically acceptable salt thereof provided in the present disclosure, A is selected from the group consisting of H, —COOH, —$NH_2$, —OH, halogen, cyano, nitro, oxo, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with $R^4$; $R^4$ is selected from the group consisting of halogen, —$NH_2$, —OH and $C_{1-6}$ alkyl.

In an alternative embodiment, in the compound of formula IV-1 or the pharmaceutically acceptable salt thereof provided in the present disclosure, A is selected from the group consisting of H, —COOH, —$NH_2$, —OH, halogen, cyano and nitro.

In an alternative embodiment, in the compound of formula IV-1 or the pharmaceutically acceptable salt thereof provided in the present disclosure, the —($CH_2$)— is unsubstituted.

In an alternative embodiment, in the compound of formula IV-1 or the pharmaceutically acceptable salt thereof provided in the present disclosure, $R^1$ is selected from $C_{1-6}$ alkyl.

In an alternative embodiment, in the compound of formula IV-1 or the pharmaceutically acceptable salt thereof provided in the present disclosure, $R^1$ is selected from $C_{1-3}$ alkyl.

In an alternative embodiment, in the compound of formula IV-1 or the pharmaceutically acceptable salt thereof provided in the present disclosure, $R^2$ is selected from $C_{1-6}$ alkyl.

In an alternative embodiment, in the compound of formula IV-1 or the pharmaceutically acceptable salt thereof provided in the present disclosure, $R^2$ is selected from $C_{1-3}$ alkyl.

In an alternative embodiment, in the compound of formula IV-1 or the pharmaceutically acceptable salt thereof provided in the present disclosure, $R^3$ is selected from $C_{1-6}$ alkyl.

In an alternative embodiment, in the compound of formula IV-1 or the pharmaceutically acceptable salt thereof provided in the present disclosure, $R^3$ is selected from $C_{1-3}$ alkyl.

In an alternative embodiment, in the compound of formula IV-1 or the pharmaceutically acceptable salt thereof provided in the present disclosure,

- $R^1$ is selected from $C_{1-6}$ alkyl;
- $R^2$ is selected from $C_{1-6}$ alkyl;
- $R^3$ is selected from $C_{1-6}$ alkyl;
- the $C_{1-6}$ alkyl is optionally further substituted with group B;
- group B is selected from the group consisting of H, —COOH, —$NH_2$, —OH, halogen, cyano, nitro and oxo.

In an alternative embodiment, in the compound of formula IV-1 or the pharmaceutically acceptable salt thereof provided in the present disclosure,

- L is —$(CH_2)_n$—;
- n is selected from the group consisting of 2 and 3;
- $R^1$ is selected from the group consisting of methyl, ethyl, n-propyl and isopropyl;
- $R^2$ is selected from the group consisting of methyl, ethyl, n-propyl and isopropyl;
- $R^3$ is selected from the group consisting of methyl, ethyl, n-propyl and isopropyl.

In an alternative embodiment, in the compound of formula IV-1 or the pharmaceutically acceptable salt thereof provided in the present disclosure, $R^1$ is selected from methyl; $R^2$ is selected from methyl; $R^3$ is selected from methyl.

Another aspect of the present disclosure provides a compound of formula V-1 or a pharmaceutically acceptable salt thereof,

V-1

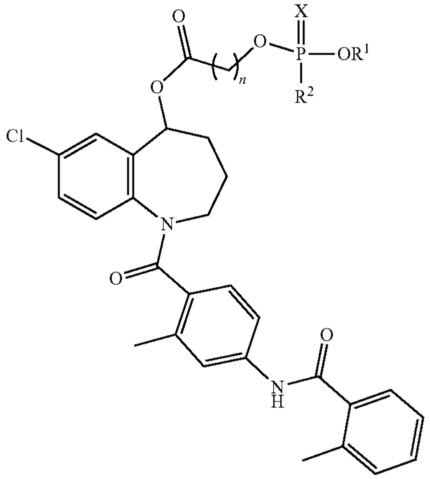

wherein,

- n is an integer selected from the group consisting of 1-10;
- X is selected from the group consisting of O and S;
- $R^1$ is selected from the group consisting of H and a hydroxy protecting group;
- $R^2$ is selected from the group consisting of hydroxy, hydroxy optionally protected by a protecting group, sulfhydryl optionally protected by a protecting group, and amino optionally protected by a protecting group;
- the “hydroxy protecting group” or “protecting group” is selected $C_{1-6}$ alkyl; the $C_{1-6}$ alkyl is optionally substituted with one or more groups selected from the group consisting of OH, CN, halogen, —C(O)O$C_{1-6}$ alkyl, 6-12 membered aryl and 6-12 membered heteroaryl.

In an alternative embodiment, in the compound of formula V-1 or the pharmaceutically acceptable salt thereof provided in the present disclosure, n is an integer selected from the group consisting of 2-8.

In an alternative embodiment, in the compound of formula V-1 or the pharmaceutically acceptable salt thereof provided in the present disclosure, n is an integer selected from the group consisting of 2-5.

In an alternative embodiment, in the compound of formula V-1 or the pharmaceutically acceptable salt thereof provided in the present disclosure, X is selected from O.

In an alternative embodiment, in the compound of formula V-1 or the pharmaceutically acceptable salt thereof provided in the present disclosure, $R^1$ is selected from H.

In an alternative embodiment, in the compound of formula V-1 or the pharmaceutically acceptable salt thereof provided in the present disclosure, $R^2$ is selected from the group consisting of hydroxy and hydroxy optionally protected by a protecting group, and the protecting group is selected from $C_{1-6}$ alkyl; the $C_{1-6}$ alkyl is optionally substituted with one or more groups selected from the group consisting of OH, CN, halogen and —C(O)O$C_{1-6}$ alkyl.

In an alternative embodiment, in the compound of formula V-1 or the pharmaceutically acceptable salt thereof provided in the present disclosure, $R^2$ is selected from the group consisting of hydroxy and hydroxy optionally protected by a protecting group, and the protecting group is selected from $C_{1-6}$ alkyl; the $C_{1-6}$ alkyl is optionally substituted with one or more groups selected from the group consisting of CN and —C(O)O$C_{1-6}$ alkyl.

In an alternative embodiment, in the compound of formula V-1 or the pharmaceutically acceptable salt thereof provided in the present disclosure, $R^2$ is selected from the group consisting of hydroxy and hydroxy optionally protected by a protecting group, and the protecting group is selected from $C_{1-3}$ alkyl; the $C_{1-3}$ alkyl is optionally substituted with CN or —C(O)O$C_{1-3}$ alkyl.

In an alternative embodiment, in the compound of formula V-1 or the pharmaceutically acceptable salt thereof provided in the present disclosure, $R^2$ is selected from hydroxy.

In an alternative embodiment, in the compound of formula V-1 or the pharmaceutically acceptable salt thereof provided in the present disclosure, the compound of formula V-1 is selected from:

10

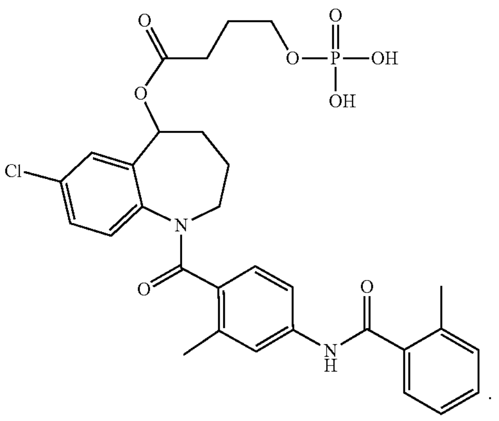

Another aspect of the present disclosure provides a compound of formula VI-1 or a pharmaceutically acceptable salt thereof,

VI-1

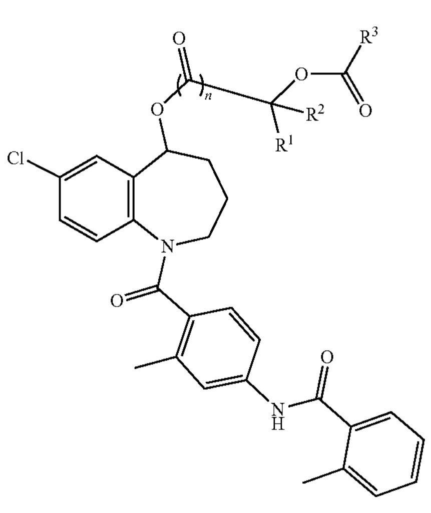

wherein, n is selected from the group consisting of 0 and 1;

$R^1$ and $R^2$ are each independently selected from the group consisting of H and A;

$R^3$ is selected from the group consisting of mPEG, $C_{1-6}$ alkyl, $C_{2-6}$ alkenyl, $C_{1-6}$ alkoxy, $C_{3-8}$ cycloalkyl and 3-12 membered heterocyclyl; the $C_{1-6}$ alkyl, $C_{2-6}$ alkenyl, $C_{1-6}$ alkoxy, $C_{3-8}$ cycloalkyl and 3-12 membered heterocyclyl are optionally substituted with A;

A is selected from the group consisting of H, —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$; the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —COOH, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VI-1 or the pharmaceutically acceptable salt thereof provided in the present disclosure, $R^1$ and $R^2$ are each independently selected from H.

In an alternative embodiment, in the compound of formula VI-1 or the pharmaceutically acceptable salt thereof provided in the present disclosure, $R^3$ is selected from the group consisting of mPEG, $C_{1-6}$ alkyl and $C_{2-6}$ alkenyl; the $C_{1-6}$ alkyl and $C_{2-6}$ alkenyl are optionally substituted with A.

In an alternative embodiment, in the compound of formula VI-1 or the pharmaceutically acceptable salt thereof provided in the present disclosure, $R^3$ is selected from the group consisting of mPEG and $C_{1-6}$ alkyl; the $C_{1-6}$ alkyl is optionally substituted with A.

In an alternative embodiment, in the compound of formula VI-1 or the pharmaceutically acceptable salt thereof provided in the present disclosure, A is selected from the group consisting of H, —COOH, —$NH_2$, —OH, halogen, cyano, nitro, $C_{1-6}$ alkyl and $C_{1-6}$ alkoxy; the $C_{1-6}$ alkyl and $C_{1-6}$ alkoxy are optionally substituted with $R^4$.

In an alternative embodiment, in the compound of formula VI-1 or the pharmaceutically acceptable salt thereof provided in the present disclosure, A is selected from the group consisting of H, —COOH, —$NH_2$, —OH, $C_{1-6}$ alkyl and $C_{1-6}$ alkoxy; the $C_{1-6}$ alkyl and $C_{1-6}$ alkoxy are optionally substituted with $R^4$.

In an alternative embodiment, in the compound of formula VI-1 or the pharmaceutically acceptable salt thereof provided in the present disclosure, A is selected from the group consisting of H, —COOH, —$NH_2$, —OH, $C_{1-6}$ alkyl and $C_{1-6}$ alkoxy; the $C_{1-6}$ alkyl and $C_{1-6}$ alkoxy are optionally substituted with $R^4$.

In an alternative embodiment, in the compound of formula VI-1 or the pharmaceutically acceptable salt thereof provided in the present disclosure, $R^4$ is selected from the group consisting of halogen, —COOH, —$NH_2$, —OH, $C_{1-6}$ alkyl and $C_{1-6}$ alkoxy; the $C_{1-6}$ alkyl and $C_{1-6}$ alkoxy are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VI-1 or the pharmaceutically acceptable salt thereof provided in the present disclosure, $R^4$ is selected from the group consisting of halogen, —COOH, —$NH_2$, —OH, $C_{1-6}$ alkyl and $C_{1-6}$ alkoxy.

In an alternative embodiment, in the compound of formula VI-1 or the pharmaceutically acceptable salt thereof provided in the present disclosure, $R^4$ is selected from the group consisting of —COOH, —$NH_2$ and —OH.

In an alternative embodiment, in the compound of formula VI-1 or the pharmaceutically acceptable salt thereof provided in the present disclosure, the compound of formula VI-1 is selected from the group consisting of:

11

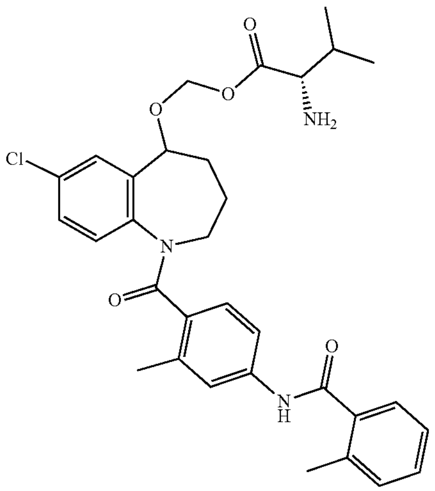

,

12

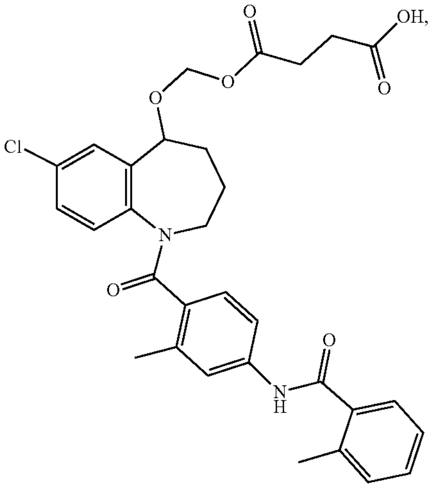

-continued

13

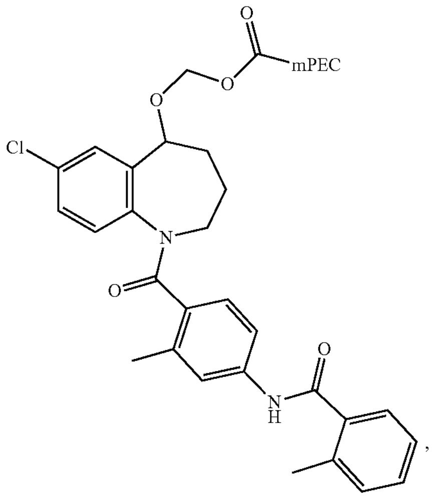

, and

14

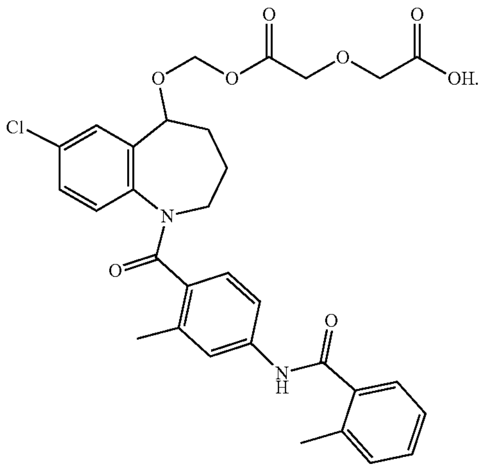

Another aspect of the present disclosure provides a compound of formula VII-1 or a pharmaceutically acceptable salt thereof,

VII-1

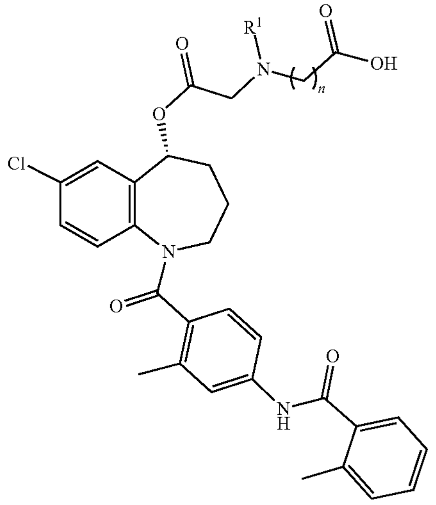

wherein, n is selected from the group consisting of 0, 1, 2, 3 and 4;

$R^1$ is selected from the group consisting of $C_{1-6}$ alkyl, $C_{2-6}$ alkenyl, $C_{1-6}$ alkoxy, $C_{3-8}$ cycloalkyl and 3-12 membered heterocyclyl; the $C_{1-6}$ alkyl, $C_{2-6}$ alkenyl, $C_{1-6}$ alkoxy, $C_{3-8}$ cycloalkyl and 3-12 membered heterocyclyl are optionally substituted with A;

A is selected from the group consisting of H, —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$; the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VII-1 or the pharmaceutically acceptable salt thereof provided in the present disclosure, $R^1$ is selected from the group consisting of $C_{1-6}$ alkyl and $C_{2-6}$ alkenyl; the $C_{1-6}$ alkyl and $C_{2-6}$ alkenyl are optionally substituted with A;

A is selected from the group consisting of H, —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$; the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VII-1 or the pharmaceutically acceptable salt thereof provided in the present disclosure, $R^1$ is selected from the group consisting of $C_{1-6}$ alkyl and $C_{2-6}$ alkenyl; the $C_{1-6}$ alkyl and $C_{2-6}$ alkenyl are optionally substituted with A;

A is selected from the group consisting of H, —COOH, —$NH_2$, —OH, halogen, cyano, nitro, oxo, $C_{1-6}$ alkyl and $C_{1-6}$ alkoxy.

In an alternative embodiment, in the compound of formula VII-1 or the pharmaceutically acceptable salt thereof provided in the present disclosure, $R^1$ is selected from $C_{1-6}$ alkyl; the $C_{1-6}$ alkyl is optionally substituted with A; A is selected from the group consisting of H, —COOH, —$NH_2$, —OH, halogen, cyano, nitro, oxo, $C_{1-6}$ alkyl and $C_{1-6}$ alkoxy.

In an alternative embodiment, in the compound of formula VII-1 or the pharmaceutically acceptable salt thereof provided in the present disclosure, $R^1$ is selected from $C_{1-6}$ alkyl; the $C_{1-6}$ alkyl is optionally substituted with A; A is selected from the group consisting of H, —COOH, —$NH_2$, —OH and halogen.

In an alternative embodiment, in the compound of formula VII-1 or the pharmaceutically acceptable salt thereof provided in the present disclosure, $R^1$ is selected from $C_{1-3}$ alkyl; the $C_{1-3}$ alkyl is optionally substituted with A; A is selected from the group consisting of H, —COOH, —$NH_2$, —OH and halogen.

In an alternative embodiment, in the compound of formula VII-1 or the pharmaceutically acceptable salt thereof provided in the present disclosure, $R^1$ is selected from $C_{1-3}$ alkyl.

In an alternative embodiment, in the compound of formula VII-1 or the pharmaceutically acceptable salt thereof provided in the present disclosure, $R^1$ is selected from the group consisting of methyl, ethyl, n-propyl and isopropyl.

In an alternative embodiment, in the compound of formula VII-1 or the pharmaceutically acceptable salt thereof provided in the present disclosure, the compound of formula VII-1 is selected from:

15

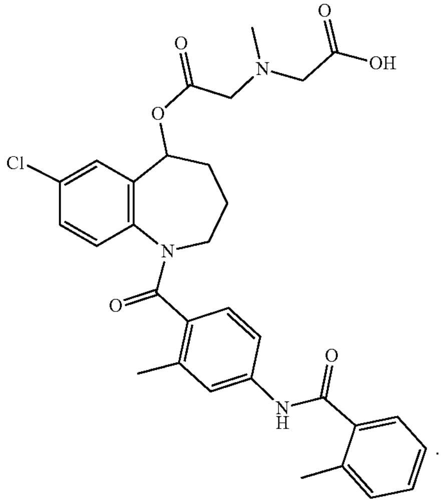

Another aspect of the present disclosure provides a compound of formula VIII-1 or a pharmaceutically acceptable salt thereof,

VIII-1

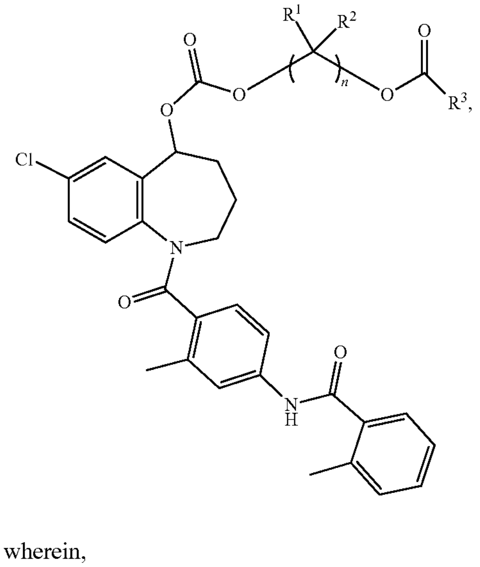

wherein, n is selected from the group consisting of 0, 1, 2, 3 and 4;

$R^1$ and $R^2$ are each independently selected from the group consisting of H and A;

$R^3$ is selected from the group consisting of mPEG, $C_{1-6}$ alkyl, $C_{2-6}$ alkenyl, $C_{1-6}$ alkoxy, $C_{3-8}$ cycloalkyl and 3-12 membered heterocyclyl; the $C_{1-6}$ alkyl, $C_{2-6}$ alkenyl, $C_{1-6}$ alkoxy, $C_{3-8}$ cycloalkyl and 3-12 membered heterocyclyl are optionally substituted with A; and when $R^3$ is selected from methyl, $R^3$ is substituted with A;

A is selected from the group consisting of —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$; the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —COOH, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VIII-1 or the pharmaceutically acceptable salt thereof provided in the present disclosure, $R^1$ and $R^2$ are each independently selected from H.

In an alternative embodiment, in the compound of formula VIII-1 or the pharmaceutically acceptable salt thereof provided in the present disclosure, $R^3$ is selected from the group consisting of mPEG, $C_{1-6}$ alkyl and $C_{2-6}$ alkenyl; the $C_{1-6}$ alkyl and $C_{2-6}$ alkenyl are optionally substituted with A;

A is selected from the group consisting of —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$; the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —COOH, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VIII-1 or the pharmaceutically acceptable salt thereof provided in the present disclosure, $R^3$ is selected from the group consisting of mPEG and $C_{1-6}$ alkyl; the $C_{1-6}$ alkyl is optionally substituted with A;

A is selected from the group consisting of —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$;

the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —COOH, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VIII-1 or the pharmaceutically acceptable salt thereof provided in the present disclosure, A is selected from the group consisting of —COOH, —$NH_2$, —OH, halogen, cyano, nitro, $C_{1-6}$ alkyl and $C_{1-6}$ alkoxy; the $C_{1-6}$ alkyl and $C_{1-6}$ alkoxy are optionally substituted with $R^4$; $R^4$ is selected from the group consisting of halogen, —COOH, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VIII-1 or the pharmaceutically acceptable salt thereof provided in the present disclosure, A is selected from the group consisting of —COOH, —$NH_2$, —OH, $C_{1-6}$ alkyl and $C_{1-6}$ alkoxy; the $C_{1-6}$ alkyl and $C_{1-6}$ alkoxy are optionally substituted with $R^4$; $R^4$ is selected from the group consisting of halogen, —COOH, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VIII-1 or the pharmaceutically acceptable salt thereof provided in the present disclosure, $R^4$ is selected from the group consisting of halogen, —COOH, —$NH_2$, —OH, $C_{1-6}$ alkyl and $C_{1-6}$ alkoxy; the $C_{1-6}$ alkyl and $C_{1-6}$ alkoxy are optionally substituted with one or more groups selected from the group consisting of —COOH, —$NH_2$, —OH, halogen, cyano, nitro, oxo, $C_{1-6}$ alkyl and $C_{1-6}$ alkoxy.

In an alternative embodiment, in the compound of formula VIII-1 or the pharmaceutically acceptable salt thereof provided in the present disclosure, $R^4$ is selected from the group consisting of halogen, —COOH, —$NH_2$, —OH, $C_{1-6}$ alkyl and $C_{1-6}$ alkoxy.

In an alternative embodiment, in the compound of formula VIII-1 or the pharmaceutically acceptable salt thereof provided in the present disclosure, $R^4$ is selected from the group consisting of —COOH, —$NH_2$ and —OH.

In an alternative embodiment, in the compound of formula VIII-1 or the pharmaceutically acceptable salt thereof provided in the present disclosure, the compound of formula VIII-1 is selected from:

16

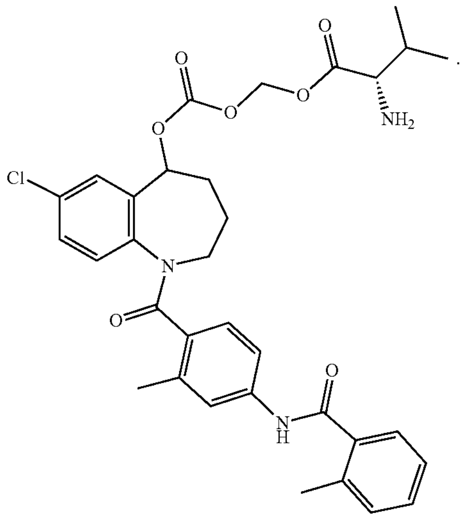

The present disclosure also provides an isotopically substituted form of the compound of formula I-1, II-1, III-1, IV-1, V-1, VI-1, VII-1 or VIII-1 or the pharmaceutically acceptable salt thereof.

In some embodiments, the isotopic substitution is a substitution with a deuterium atom.

The present disclosure also provides a pharmaceutical composition comprising at least one of the compounds of formulas I-1, II-1, III-1, IV-1, V-1, VI-1, VII-1 and VIII-1 or the pharmaceutically acceptable salts thereof or the isotopically substituted forms thereof described above, and a pharmaceutically acceptable excipient.

In some embodiments, a unit dose of the pharmaceutical composition is 0.001 mg-1000 mg.

In certain embodiments, the pharmaceutical composition comprises 0.01-99.99% of the compound of formula I-1, II-1, III-1, IV-1, V-1, VI-1, VII-1 or VIII-1 or the pharmaceutically acceptable salt thereof or the isotopically substituted form thereof described above, on the basis of the total weight of the composition.

In certain embodiments, the pharmaceutical composition comprises 0.1-99.9% of the compound of formula I-1, II-1, III-1, IV-1, V-1, VI-1, VII-1 or VIII-1 or the pharmaceutically acceptable salt thereof or the isotopically substituted form thereof described above, on the basis of the total weight of the composition.

In certain embodiments, the pharmaceutical composition comprises 0.5%-99.5% of the compound of formula I-1, II-1, III-1, IV-1, V-1, VI-1, VII-1 or VIII-1 or the pharmaceutically acceptable salt thereof or the isotopically substituted form thereof described above, on the basis of the total weight of the composition.

In certain embodiments, the pharmaceutical composition comprises 1%-99% of the compound of formula I-1, II-1, III-1, IV-1, V-1, VI-1, VII-1 or VIII-1 or the pharmaceutically acceptable salt thereof or the isotopically substituted form thereof described above, on the basis of the total weight of the composition.

In certain embodiments, the pharmaceutical composition comprises 2%-98% of the compound of formula I-1, II-1, III-1, IV-1, V-1, VI-1, VII-1 or VIII-1 or the pharmaceutically acceptable salt thereof or the isotopically substituted form thereof described above, on the basis of the total weight of the composition.

In certain embodiments, the pharmaceutical composition comprises 0.01%-99.99% of a pharmaceutically acceptable excipient, on the basis of the total weight of the composition.

In certain embodiments, the pharmaceutical composition comprises 0.1%-99.9% of a pharmaceutically acceptable excipient, on the basis of the total weight of the composition.

In certain embodiments, the pharmaceutical composition comprises 0.5%-99.5% of a pharmaceutically acceptable excipient, on the basis of the total weight of the composition.

In certain embodiments, the pharmaceutical composition comprises 1%-99% of a pharmaceutically acceptable excipient, on the basis of the total weight of the composition.

In certain embodiments, the pharmaceutical composition comprises 2%-98% of a pharmaceutically acceptable excipient, on the basis of the total weight of the composition.

The compounds provided in the present disclosure have, for example, vasopressin antagonism, vasodilating activity, hypotensive activity, activity for inhibiting saccharide release in the liver, activity for inhibiting mesangial cell growth, aquaretic activity, and activity for inhibiting platelet aggregation.

The compounds provided in the present disclosure are useful as vasodilators, hypotensive agents, aquaretic agents, and platelet aggregation inhibitors.

The present disclosure also provides a method for preventing and/or treating a patient having a disease associated with vasopressin receptors, which comprises administering to the patient a therapeutically effective amount of the compound of formula I-1, II-1, III-1, IV-1, V-1, VI-1, VII-1 or VIII-1 or the pharmaceutically acceptable salt thereof or the isotopically substituted form thereof described above or the pharmaceutical composition described above.

The present disclosure also provides a method for preventing and/or treating a patient having hypertension, edema (e.g., cardiac edema, hepatic edema, renal edema or cerebral edema), abdominal dropsy, heart failure (e.g., severe heart failure), renal dysfunction, syndrome of inappropriate vasopressin secretion (SIADH), cirrhosis, hyponatremia, hypokalemia, diabetes, circulatory insufficiency, polycystic kidney disease (PKD), cerebral infarction or myocardial infarction, which comprises administering to the patient a therapeutically effective amount of the compound of formula I-1, II-1, III-1, IV-1, V-1, VI-1, VII-1 or VIII-1 or the pharmaceutically acceptable salt thereof or the isotopically substituted form thereof described above or the pharmaceutical composition described above.

The present disclosure also provides use of the compound of formula I-1, II-1, III-1, IV-1, V-1, VI-1, VII-1 or VIII-1 or the pharmaceutically acceptable salt thereof or the isotopically substituted form thereof described above or the pharmaceutical composition described above in the preparation of a medicament for preventing and/or treating a disease associated with vasopressin receptors.

The present disclosure also provides use of the compound of formula I-1, II-1, III-1, IV-1, V-1, VI-1, VII-1 or VIII-1 or the pharmaceutically acceptable salt thereof or the isotopically substituted form thereof described above or the pharmaceutical composition described above in the preparation of a medicament for preventing and/or treating hypertension, edema (e.g., cardiac edema, hepatic edema, renal edema or cerebral edema), abdominal dropsy, heart failure (e.g., severe heart failure), renal dysfunction, syndrome of inappropriate vasopressin secretion (SIADH), cirrhosis, hyponatremia, hypokalemia, diabetes, circulatory insufficiency, polycystic kidney disease (PKD), cerebral infarction or myocardial infarction.

The present disclosure also provides the compound of formula I-1, II-1, III-1, IV-1, V-1, VI-1, VII-1 or VIII-1 or the pharmaceutically acceptable salt thereof or the isotopically substituted form thereof described above or the pharmaceutical composition described above for use in the prevention and/or treatment of a disease associated with vasopressin receptors.

The present disclosure also provides the compound of formula I-1, II-1, III-1, IV-1, V-1, VI-1, VII-1 or VIII-1 or the pharmaceutically acceptable salt thereof or the isotopically substituted form thereof described above or the pharmaceutical composition described above for use in the prevention and/or treatment of hypertension, edema (e.g., cardiac edema, hepatic edema, renal edema or cerebral edema), abdominal dropsy, heart failure (e.g., severe heart failure), renal dysfunction, syndrome of inappropriate vasopressin secretion (SIADH), cirrhosis, hyponatremia, hypokalemia, diabetes, circulatory insufficiency, polycystic kidney disease (PKD), cerebral infarction or myocardial infarction.

In another aspect, the pharmaceutically acceptable salt of the compound in the present disclosure is selected from the group consisting of an inorganic salt and an organic salt.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomer, (L)-isomer, and racemic mixtures and other mixtures thereof, such as enantiomerically or diastereomerically enriched mixtures. all these isomers and mixtures thereof fall within the scope of the present disclosure. Asymmetric carbon atoms may be present in substituents such as alkyl. The compounds of the present disclosure containing asymmetric carbon atoms can be isolated in optically active pure form or in racemic form. The optically active pure form can be isolated from a racemic mixture or synthesized using chiral starting materials or chiral reagents.

Optically active (R)- and (S)-enantiomers, and (D)- and (L)-isomers can be prepared by chiral synthesis, chiral reagents or other conventional techniques. If one enantiomer of a certain compound of the present disclosure is desired, it may be prepared by asymmetric synthesis or derivatization with a chiral auxiliary, wherein the resulting mixture of diastereomers is isolated and the auxiliary group is cleaved to provide the pure desired enantiomer. Alternatively, when the molecule contains a basic functional group (e.g., amino) or an acidic functional group (e.g., carboxyl), salts of diastereomers are formed with an appropriate optically active acid or base, followed by resolution of diastereomers by conventional methods known in the art, and the pure enantiomers are obtained by recovery. In addition, separation of enantiomers and diastereomers is generally accomplished by chromatography using a chiral stationary phase, optionally in combination with chemical derivatization (e.g., carbamate formation from amines).

In the chemical structure of the compound of the present disclosure, a bond “ ” represents an unspecified configuration—that is, if chiral isomers exist in the chemical structure, the bond “ ” may be “ ” or “ ”, or contains both the configurations of “ ” and “ ”. The bond “ ” represents an unspecified configuration, including the cis (E) or trans (Z) configuration.

The compounds and intermediates of the present disclosure may also exist in different tautomeric forms, and all such forms are included within the scope of the present disclosure. The term “tautomer” or “tautomeric form” refers to structural isomers of different energies that can interconvert via a low energy barrier. For example, proton tautomers (also known as proton transfer tautomers) include interconversion via proton migration, such as keto-enol and imine-enamine, lactam-lactim isomerization. An example of a lactam-lactim equilibrium is present between A and B as shown below.

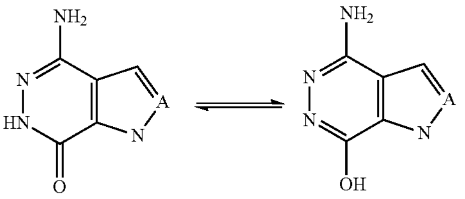

A B

All tautomeric forms are within the scope of the present disclosure. The nomenclature of the compounds does not exclude any tautomers.

The present disclosure also includes isotopically-labeled compounds which are identical to those recited herein but have one or more atoms replaced by an atom having an atomic mass or mass number different from the atomic mass or mass number usually found in nature. Examples of isotopes that can be incorporated into the compound of the present disclosure include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Unless otherwise specified, when a position is specifically assigned deuterium (D), the position should be construed as deuterium with an abundance that is at least 1000 times greater than the natural abundance of deuterium (which is 0.015%) (i.e., at least 10% deuterium incorporation). The compounds of examples comprise deuterium having an abundance that is greater than at least 1000 times the natural abundance, at least 2000 times the natural abundance, at least 3000 times the natural abundance, at least 4000 times the natural abundance, at least 5000 times the natural abundance, at least 6000 times the natural abundance, or higher times the natural abundance. The present disclosure further comprises various deuterated forms of the compounds. Each available hydrogen atom connected to a carbon atom may be independently replaced by a deuterium atom. Those skilled in the art are able to synthesize the deuterated forms of the compound of formula (I) with reference to the relevant literature. Commercially available deuterated starting materials can be used in preparing the deuterated forms of the compound of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like.

Terms and Definitions

“Alkyl” refers to a saturated aliphatic hydrocarbon group, including linear and branched groups of 1 to 20 carbon atoms, preferably alkyl having 1 to 12 carbon atoms, and more preferably alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl and various branched isomers thereof, and the like. The alkyl may be substituted or unsubstituted, and when it is substituted, the substituent may be substituted at any available point of attachment, and the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "alkenyl" refers to an alkyl group containing at least one carbon-carbon double bond in the molecule, wherein the alkyl is as defined above, and it has alkenyl of 2 to 12 (e.g., 2, 3, 4, 5, 6, 7, 8, 9, 10, 11, and 12) carbon atoms (i.e., $C_{2-12}$ alkenyl).

Examples of alkenyl include, but are not limited to, ethenyl, allyl, 1-propenyl, 1-butenyl, 2-butenyl, 3-butenyl, 2-methylbut-2-enyl, 3-methylbut-1-enyl, 1-pentenyl, 3-pentenyl, and 4-hexenyl. The alkenyl may be substituted or unsubstituted, and when it is substituted, the substituent may be substituted at any available point of attachment, and the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "alkynyl" refers to an alkyl group containing at least one carbon-carbon triple bond in the molecule, wherein the alkyl is as defined above, and it has 2 to 12 (e.g., 2, 3, 4, 5, 6, 7, 8, 9, 10, 11, and 12) carbon atoms (i.e., $C_{2-12}$ alkynyl). e.g., ethynyl, propynyl (e.g., 1-propynyl, 2-propynyl), 3-butynyl, pentynyl, hexynyl and 1-methylpent-2-ynyl.

The alkynyl may be substituted or unsubstituted, and when it is substituted, the substituent may be substituted at any available point of attachment, and the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "cycloalkyl" refers to a saturated or partially unsaturated monocyclic or polycyclic hydrocarbon substituent. The cycloalkyl contains 3 to 20 carbon atoms, preferably 3 to 12 carbon atoms, more preferably 3 to 8 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. The polycyclic cycloalkyl includes spiro cycloalkyl, fused cycloalkyl and bridged cycloalkyl.

The cycloalkyl may be fused to aryl, heteroaryl or heterocyclyl, wherein the ring attached to the parent structure is cycloalkyl; non-limiting examples include indanyl, tetrahydronaphthyl, benzocycloheptyl, and the like. The cycloalkyl may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "heterocyclyl" refers to a saturated or partially unsaturated monocyclic or polycyclic hydrocarbon substituent containing 3 to 20 ring atoms, one or more of which are heteroatoms selected from the group consisting of nitrogen, oxygen and $S(O)_m$ (where m is an integer of 0 to 2), excluding a ring moiety of —O—O—, —O—S— or —S—S—, and the remaining ring atoms are carbon atoms. The heterocyclyl preferably contains 3 to 12 ring atoms, of which 1 to 4 are heteroatoms; and more preferably contains 3 to 8 ring atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, etc. Polycyclic heterocyclyl includes spiro heterocyclyl, fused heterocyclyl, and bridged heterocyclyl. Non-limiting examples of polycyclic heterocyclyl include:

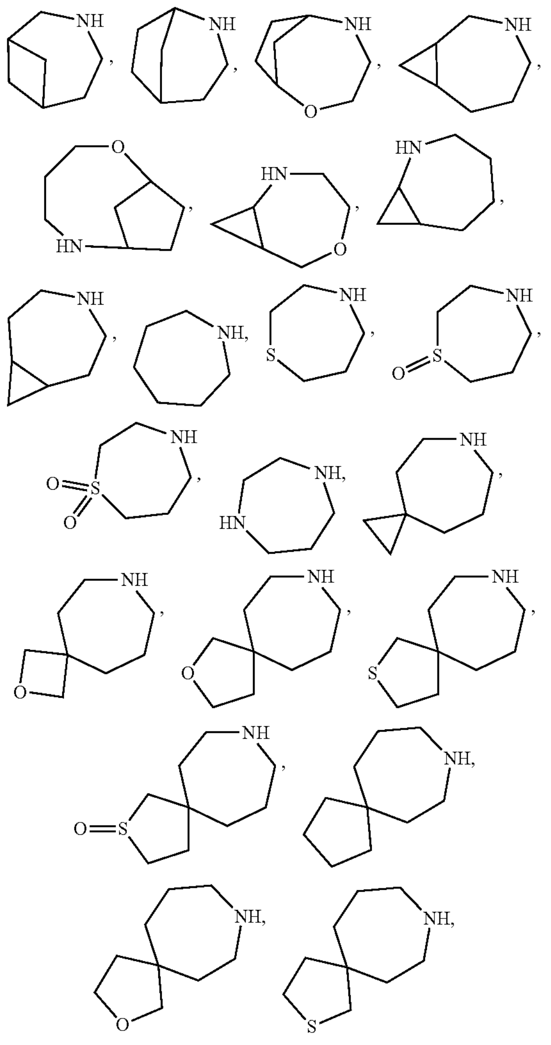

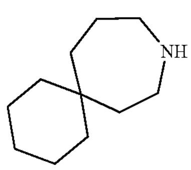

and

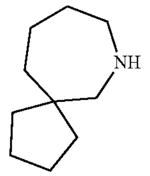

and the like.

The heterocyclyl may be fused to aryl, heteroaryl or cycloalkyl, wherein the ring attached to the parent structure is heterocyclyl; its non-limiting examples include:

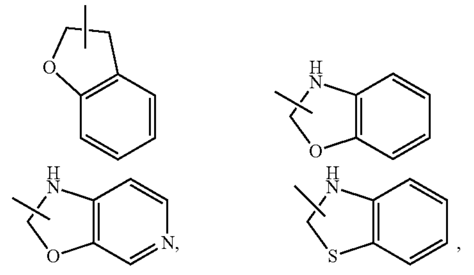

etc.

The heterocyclyl may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "aryl" refers to a 6- to 14-membered, preferably 6- to 12-membered, carbon monocyclic or fused polycyclic (i.e., rings sharing a pair of adjacent carbon atoms) group having a conjugated π-electron system, such as phenyl and naphthyl. The aryl ring may be fused to heteroaryl, heterocyclyl or cycloalkyl, wherein the ring attached to the parent structure is aryl; its non-limiting examples include:

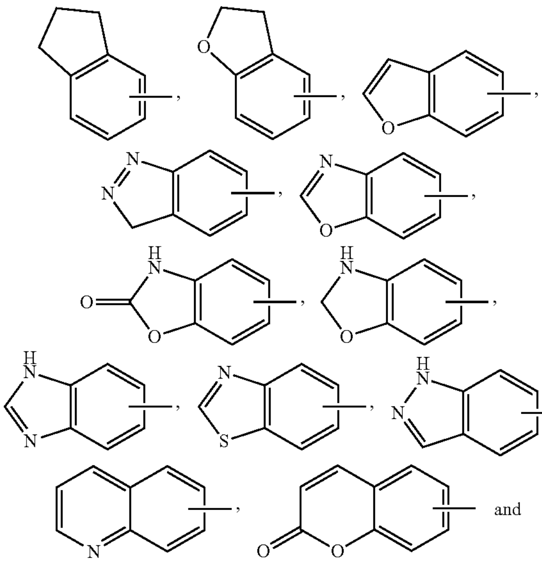

and

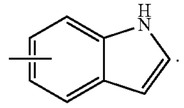

The aryl may be substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "heteroaryl" refers to a heteroaromatic system containing 1 to 4 heteroatoms and 5 to 14 ring atoms, wherein the heteroatoms are selected from the group consisting of oxygen, sulfur and nitrogen. Heteroaryl is preferably 6- to 12-membered, more preferably 5- or 6-membered. Its non-limiting examples include: imidazolyl, furyl, thienyl, thiazolyl, pyrazolyl, oxazolyl, pyrrolyl, tetrazolyl, pyridinyl, pyrimidinyl, thiadiazole, pyrazine,

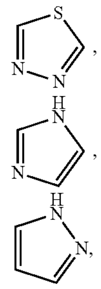

and the like.

The heteroaryl may be fused to aryl, heterocyclyl or cycloalkyl, wherein the ring attached to the parent structure is heteroaryl; its non-limiting examples include:

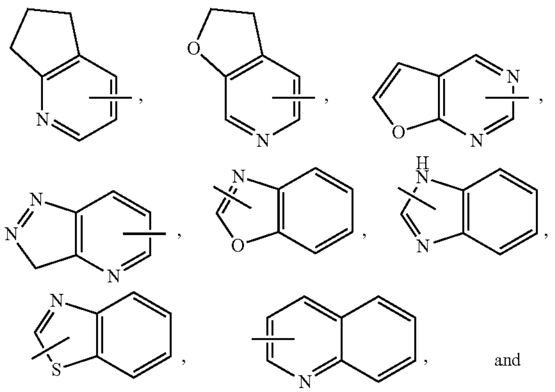

and

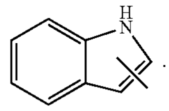

The heteroaryl may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The term "alkoxy" refers to —O-(alkyl), wherein the alkyl is as defined above. Non-limiting examples of alkoxy include: methoxy, ethoxy, propoxy, butoxy, cyclopropyloxy, cyclobutoxy, cyclopentyloxy and cyclohexyloxy. The alkoxy may be optionally substituted or unsubstituted, and when it is substituted, the substituent is preferably one or more groups independently selected from the group consisting of halogen, hydroxy, oxo, nitro, cyano, $C_{1-6}$ alkyl, $C_{1-6}$ alkoxy, $C_{3-8}$ cycloalkyl and 3-12 membered heterocyclyl.

The "hydroxy protecting group" of the present disclosure is a group known in the art for hydroxy protection; see the literature ("Protective Groups in Organic Synthesis", $5^{Th}$ Ed. T. W. Greene & P. G. M. Wuts) for the hydroxy protecting groups. As an example, including but not limited to being as an example, preferably, the hydroxy protecting group may be ($C_{1-10}$ alkyl or aryl)$_3$silyl, e.g., triethylsilyl, triisopropylsilyl, tert-butyldimethylsilyl, tert-butyldiphenylsilyl, or the like; $C_{1-10}$ alkyl or substituted alkyl, e.g., methyl, tert-butyl, allyl, benzyl, methoxymethyl, ethoxyethyl, 2-tetrahydropyranyl (THP), or the like; ($C_{1-10}$alkyl or aryl)acyl, e.g., formyl, acetyl, benzoyl, or the like; ($C_{1-6}$ alkyl or $C_{6-10}$ aryl)sulfonyl; or ($C_{1-6}$ alkoxy or $C_{6-10}$ aryloxy)carbonyl; or acetyl (Ac), 2-methoxyethoxymethyl ether (MEM), methoxymethyl ether (MOM), p-methoxybenzyl ether (PMB) or methylthiomethyl ether (MTM).

The term "hydroxy" refers to the —OH group.

The term "halogen" refers to fluorine, chlorine, bromine or iodine.

The term "amino" refers to $—NH_2$.

The term "cyano" refers to —CN.

The term "nitro" refers to $—NO_2$.

The term "oxo" refers to the =O substituent.

"Optional" or "optionally" means that the event or circumstance subsequently described may, but does not necessarily, occur, and that the description includes instances where the event or circumstance occurs or does not occur. For example, "heterocyclyl optionally substituted with alkyl" means that the alkyl may, but does not necessarily, exist, and that the description includes instances where the heterocyclyl is or is not substituted with the alkyl.

"Substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue effort.

The term "pharmaceutical composition" refers to a mixture containing one or more of the compounds described herein or a pharmaceutically acceptable salt or pro-drug thereof, and other chemical components, and other components, for example, pharmaceutically acceptable carriers and excipients. The pharmaceutical composition is intended to promote the administration to an organism, so as to facilitate the absorption of the active ingredient, thereby exerting biological activity.

DETAILED DESCRIPTION

Figure 1:
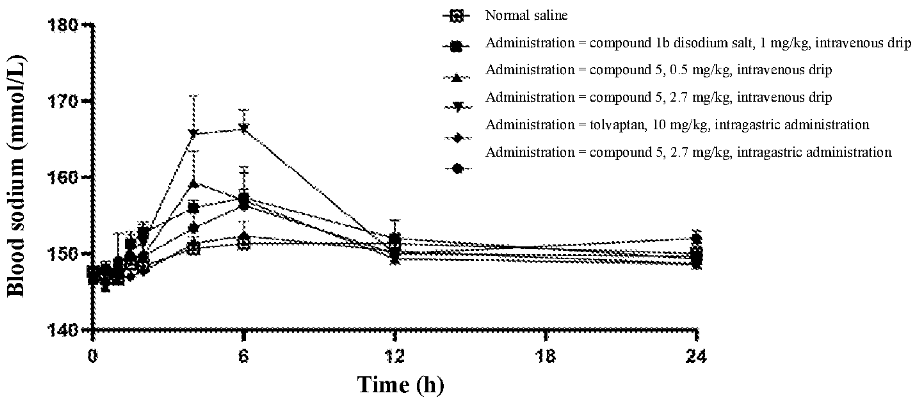
FIG. 1 shows blood sodium curves of the compounds of the present invention in beagles.

The present disclosure is further described below with reference to examples, which are not intended to limit the scope of the present disclosure.

Experimental procedures without conditions specified in the examples of the present disclosure were generally conducted according to conventional conditions, or according to conditions recommended by the manufacturers of the starting materials or commercial products. Reagents without origins specified are commercially available conventional reagents.

The structures of the compounds were determined by nuclear magnetic resonance (NMR) spectroscopy and/or mass spectrometry (MS).

NMR shifts (δ) were given in $10^{-6}$ (ppm). NMR analysis was performed on a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as solvents and tetramethylsilane (TMS) as an internal standard.

MS analysis was performed on an Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: waters, MS model: waters ACQuity Qda Detector/Waters SQ Detector) and THERMO Ultimate 3000-Q Exactive (manufacturer: THERMO, MS model: THERMO Q Exactive).

High performance liquid chromatography (HPLC) analysis was performed using the following HPLC instruments: Agilent HPLC 1200DAD, Agilent HPLC 1200VWD and Waters HPLC e2695-2489.

Chiral HPLC analysis was performed on an Agilent 1260 DAD high performance liquid chromatograph.

Preparative high performance liquid chromatography used Waters 2545-2767, Waters 2767-SQ Detecor2, Shimadzu LC-20AP and Gilson GX-281 preparative chromatographs.

Preparative chiral chromatography used a Shimadzu LC-20AP preparative chromatograph.

The CombiFlash preparative flash chromatograph used was CombiFlash Rf200 (TELEDYNE ISCO).

Yantai Huanghai HSGF254 or Qingdao GF254 silica gel plates, 0.15-0.2 mm layer thickness, were adopted for thin-layer chromatography (TLC) analysis and 0.4-0.5 mm layer thickness for TLC separation and purification.

Silica gel column chromatography generally used 200- to 300-mesh silica gel (Huanghai, Yantai) as the carrier.

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions could all be performed in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Pressurized hydrogenation reactions were performed using a Parr 3916EKX hydrogenator and a Qinglan QL-500 hydrogenator, or an HC2-SS hydrogenator.

Hydrogenation reactions generally involve 3 cycles of vacuumization and hydrogen purging.

Microwave reactions were performed on a CEM Discover-S 908860 microwave reactor.

In the examples, a solution refers to an aqueous solution unless otherwise specified.

In the examples, the reaction temperature refers to room temperature, preferably 20° C. to 30° C., unless otherwise specified.

Example 1
Preparation of Disodium (7-chloro-1-(2-methyl-4-(2-methylbenzamido)benzoyl)-2,3,4,5-tetrahydro-benzo[b]azepine-5-oxycarbonyl)-L-glutamate (Compound 1)
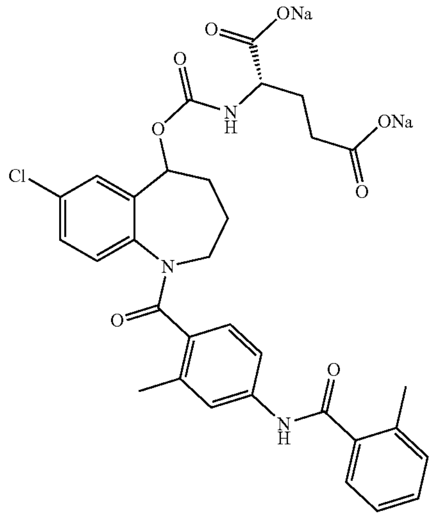
1
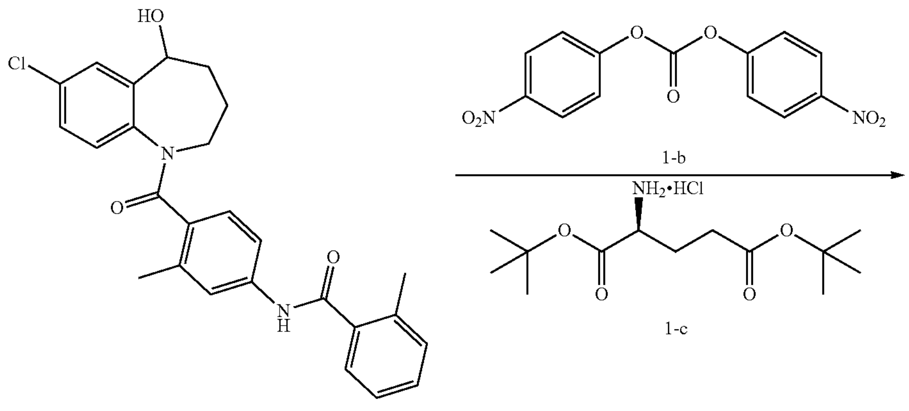
1-a
1-b
1-c -continued

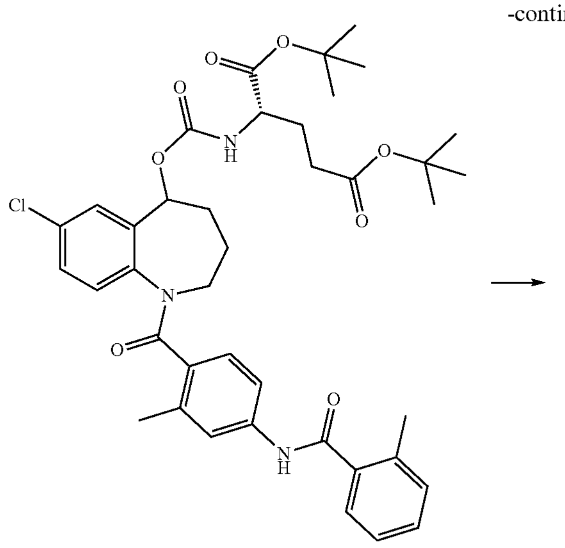

1-d

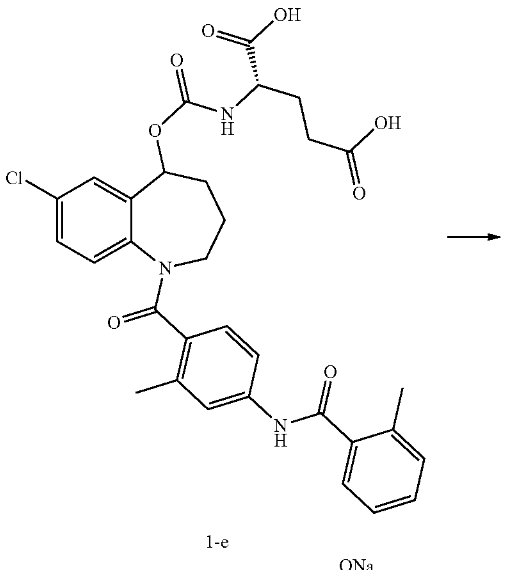

1-e

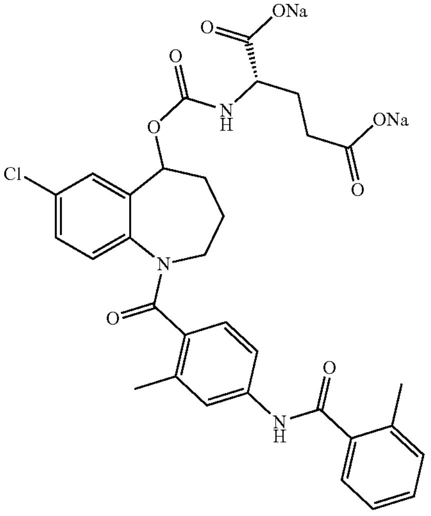

1

Step 1: Preparation of Compound 1-d

Commercially available tolvaptan 1-a (300 mg, 0.67 mmol), compound 1-b (204 mg, 0.67 mmol) and diisopropylethylamine (432 mg, 3.35 mmol) were dissolved in N,N-dimethylformamide (10 mL) in a nitrogen atmosphere, and the solution was stirred at room temperature for 3 h. Compound 1-c (297 mg, 1.005 mmol) was added, and the mixture was stirred at room temperature overnight. The reaction mixture was diluted with water and extracted with ethyl acetate. After concentration, the residue was separated and purified by column chromatography to give compound 1-d (494 mg, yield: 93.92%).

$^1$H NMR (400 MHz, DMSO-$d_6$) δ 10.45-10.15 (m, 1H), 7.86-7.65 (m, 1H), 7.60-7.51 (m, 1H), 7.46-7.33 (m, 3H), 7.33-7.24 (m, 3H), 7.18-7.08 (m, 1H), 7.01-6.58 (m, 2H), 5.96-5.60 (m, 1H), 5.00-4.52 (m, 1H), 4.08-3.92 (m, 1H), 2.84-2.72 (m, 1H), 2.43-2.31 (m, 6H), 2.30-2.21 (m, 3H), 2.21-2.11 (m, 1H), 2.07-1.92 (m, 1H), 1.89-1.67 (m, 2H), 1.59-1.47 (m, 1H), 1.41 (s, 9H), 1.40 (s, 9H).

Step 2: Preparation of Compound 1-e

Compound 1-d (394 mg, 0.88 mmol) was dissolved in dichloromethane (5 mL), and trifluoroacetic acid (1 mL) was added. The mixture was stirred at room temperature for 24 h. A saturated solution of sodium carbonate was added to adjust the pH to 9-10. The mixture was washed with dichloromethane. The aqueous phase was adjusted to pH 1-2 with a 1 mol/L hydrochloric acid solution and extracted with ethyl acetate. After concentration, the residue was purified by preparative HPLC to give compound 1-e (163 mg, yield: 48.82%).

$^1$H NMR (400 MHz, DMSO-$d_6$) δ 12.65 (br, 2H), 10.44-10.10 (m, 1H), 7.99-7.72 (m, 1H), 7.67-7.53 (m, 1H), 7.48-7.35 (m, 3H), 7.33-7.19 (m, 3H), 7.17-7.03 (m, 1H), 7.00-6.60 (m, 2H), 5.87-5.60 (m, 1H), 4.97-4.53 (m, 1H), 4.13-3.98 (m, 1H), 2.85-2.65 (m, 1H), 2.43-2.26 (m, 8H), 2.23-2.10 (m, 1H), 2.10-1.91 (m, 2H), 1.90-1.45 (m, 3H).

Step 3: Preparation of Compound 1

Sodium hydroxide (12.9 mg, 0.32 mmol) was dissolved in water (15 mL). The solution was cooled to 0° C., and a solution of compound 1-e (100 mg, 0.16 mmol) in acetonitrile (5 mL) was added dropwise with stirring. After the addition, the mixture was stirred for another 5 min. The mixture was lyophilized in vacuo to remove the solvent to give compound 1 (101 mg, yield: 94.39%).

$^1H$ NMR (400 MHz, DMSO-$d_6$) δ 10.45-10.12 (m, 1H), 7.85-7.60 (m, 1H), 7.59-7.15 (m, 7H), 7.15-7.02 (m, 1H), 7.01-6.57 (m, 2H), 5.96-5.57 (m, 1H), 5.00-4.55 (m, 1H), 3.90-3.75 (m, 1H), 2.83-2.70 (m, 1H), 2.43-2.31 (m, 6H), 2.27-2.03 (m, 3H), 2.03-1.83 (m, 2H), 1.83-1.47 (m, 3H).

MS: m/z $[M+H]^+$: 622.2.

Example 2

Preparation of 7-Chloro-1-(2-methyl-4-(2-methylbenzamido)benzoyl)-2,3,4,5-tetrahydro-1H-benzo[b]azepin-5-yl methyl((S)-pyrrolidin-2-yl)methyl)carbamate (Compound 3) hydrochloride

3

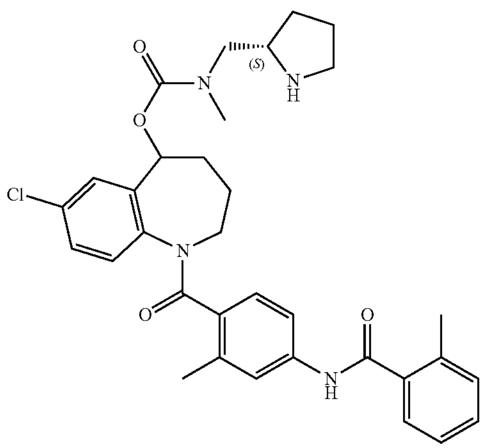

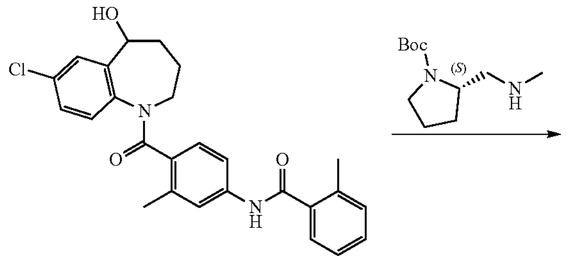

1-a

-continued

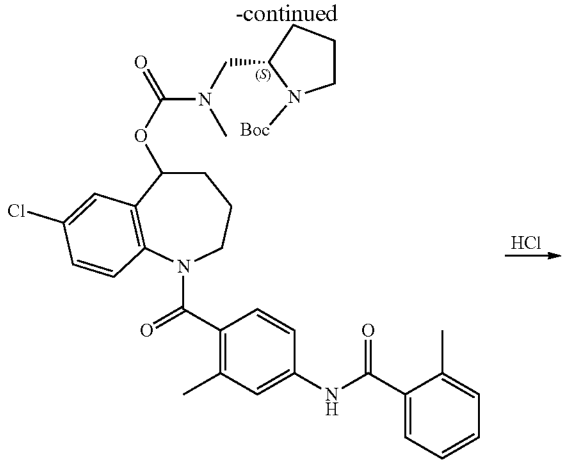

3-b

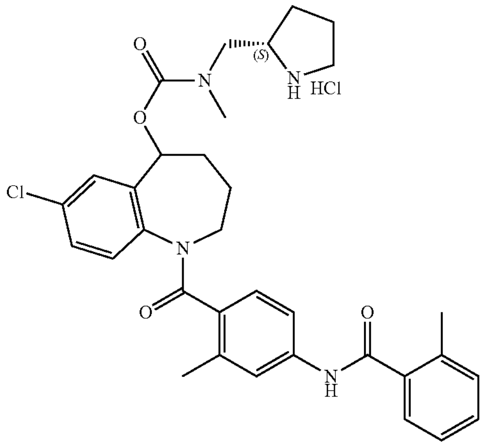

3

Step 1: Preparation of Compound 3-b

Commercially available tolvaptan 1-a (225 mg, 0.500 mmol), di(p-nitrophenyl)carbonate (175 mg, 0.580 mmol) and diisopropylethylamine (323 mg, 2.50 mmol) were weighed into a reaction flask, and dry N,N-dimethylformamide (10 mL) was added. The mixture was stirred at room temperature for 3 h in a nitrogen atmosphere. Then, tert-butyl (S)-2-((methylamino)methyl)pyrrolidine-1-carboxylate (161 mg, 0.75 mmol) was added, and the mixture was stirred at room temperature overnight. Ethyl acetate and water were added to dilute the reaction mixture. The aqueous phase was extracted with ethyl acetate. The organic phases were combined, washed with water and then with a saturated solution of sodium chloride, dried over anhydrous sodium sulfate and filtered. The filtrate was concentrated under reduced pressure. The residue was purified by reversed-phase column chromatography to give compound 3-b (280 mg, yield: 81%).

$^1H$ NMR (400 MHz, DMSO-$d_6$) δ 10.23 (s, 1H), 7.81-6.55 (m, 10H), 6.02-5.66 (m, 1H), 4.92-4.52 (m, 1H), 4.23-3.80 (m, 1H), 3.63-3.21 (m, 1H), 3.28-2.71 (m, 7H), 2.36 (s, 6H), 2.25-1.62 (m, 8H), 1.40 (s, 9H).

Step 2: Preparation of Compound 3

Compound 3-b (100 mg, 0.145 mmol) was weighed out. The system was purged with nitrogen three times, and a solution of hydrogen chloride in ethyl acetate (5.0 mL, 2.0 M) was added under an ice-water bath. The mixture was stirred at room temperature for 4 h. The reaction mixture was concentrated under reduced pressure and triturated with ethyl acetate (4.0 mL) at room temperature for 1 h. The triturate was filtered, and the filter cake was washed with ethyl acetate (1 mL) and dried under reduced pressure to give the hydrochloride of compound 3 (75 mg, yield: 82%).

$^1$H NMR (400 MHz, DMSO-$d_6$) δ 7.82-6.38 (m, 10H), 5.97-5.68 (m, 1H), 4.95-4.48 (m, 1H), 4.08-3.74 (m, 2H), 3.36-2.71 (m, 7H), 2.33 (s, 6H), 2.22-1.46 (m, 8H).

Example 3

Preparation of 7-Chloro-1-(2-methyl-4-(2-methyl-benzamido)benzoyl)-2,3,4,5-tetrahydro-benzo[b]azepin-5-(2-(trimethylammonio)ethyl)phosphate (Compound 4)

4

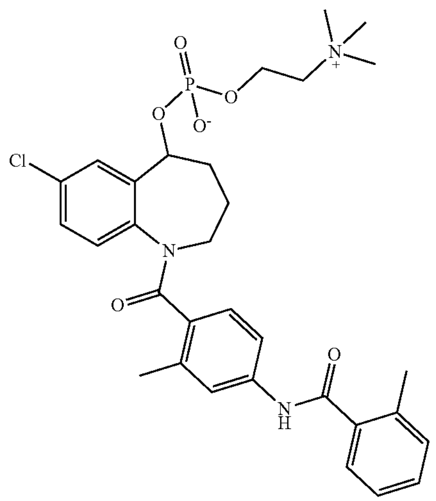

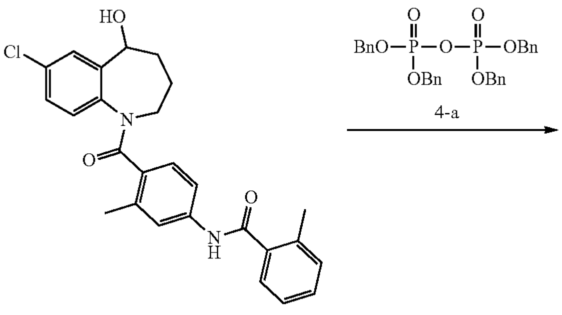

I-a 4-a

-continued

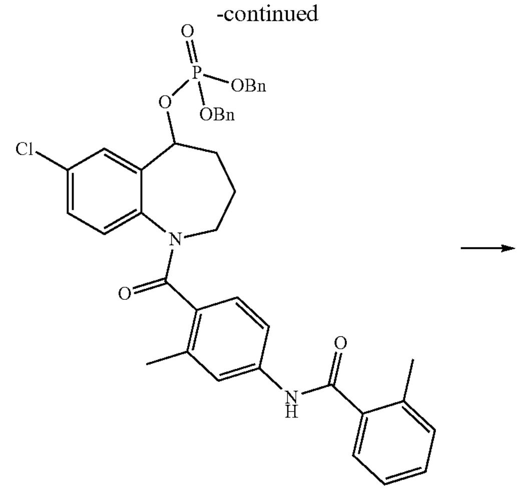

4-b

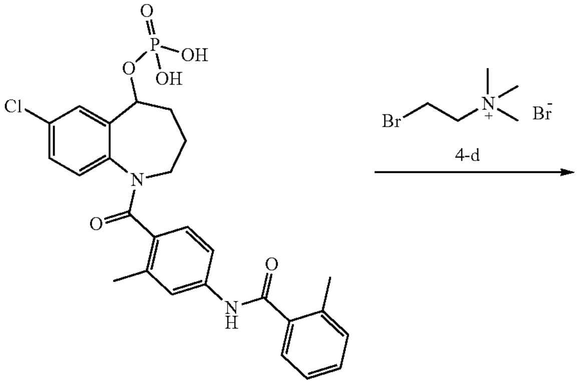

4-c 4-d

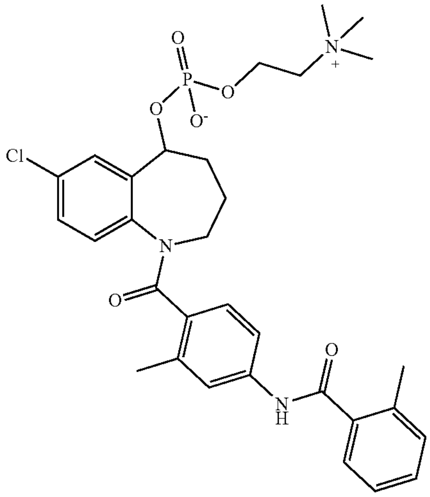

4

Step 1: Preparation of Compound 4-b

Commercially available tolvaptan 1-a (224 mg, 0.5 mmol) was dissolved in tetrahydrofuran (5 mL) in a nitrogen atmosphere, and the solution was cooled to −60° C. Lithium bis(trimethylsilyl)amide (1.5 mL, 1.5 mmol, 1 M in THF) was slowly added dropwise. After the addition, the mixture was stirred at −60° C. for 0.5 h. A solution of compound 4-a (538 mg, 1.0 mmol) in THE (2 mL) was then added dropwise. After the addition, the mixture was warmed to room temperature and allowed to react overnight. The reaction mixture was quenched with a saturated solution of ammonium chloride and extracted with ethyl acetate. The organic phase was concentrated under reduced pressure. The residue was separated and purified by column chromatography to give compound 4-b (323 mg, yield: 91.11%).

$^1$H NMR (400 MHz, DMSO-$d_6$) δ 10.44-10.14 (m, 1H), 7.81-7.45 (m, 3H), 7.45-7.21 (m, 15H), 7.20-7.00 (m, 1H), 6.87-6.62 (m, 1H), 5.72-5.45 (m, 1H), 5.17-4.96 (m, 3H), 4.94-4.46 (m, 1H), 3.52-3.37 (m, 1H), 2.85-2.69 (m, 1H), 2.45-2.25 (m, 6H), 2.25-2.08 (m, 1H), 1.95-1.45 (m, 3H).

Step 2: Preparation of Compound 4-c

Compound 4-b (323 mg, 0.46 mmol) was dissolved in dichloromethane (3 mL) and trifluoroacetic acid (6 mL). The solution was stirred at room temperature for 24 h. After concentration, the residue was diluted with ethyl acetate, and the pH was adjusted to 9-10 with a 1 mol/L solution of sodium hydroxide. The organic phase was extracted with water twice. The aqueous phases were combined, adjusted to pH 1-2 with a 1 mol/L HCl solution and extracted with ethyl acetate. The organic phase was concentrated under reduced pressure to give compound 4-c (190 mg, yield: 78.84%).

$^1$H NMR (400 MHz, DMSO-$d_6$) δ 10.44-10.18 (m, 1H), 7.80-7.52 (m, 1H), 7.49-7.35 (m, 3H), 7.34-7.24 (m, 3H), 7.22-7.12 (m, 1H), 6.90-6.61 (m, 2H), 5.54-5.25 (m, 2H), 4.94-4.55 (m, 1H), 2.84-2.64 (m, 1H), 2.43-2.19 (m, 8H), 2.04-1.48 (m, 3H).

Step 3: Preparation of Compound 4

Compound 4-c (300 mg, 0.57 mmol), compound 4-d (700 mg, 2.84 mmol) and potassium carbonate (391 mg, 2.84 mmol) were dissolved in N,N-dimethylformamide (20 mL), and the reaction was heated at 90° C. for 24 h. The reaction mixture was concentrated under reduced pressure. The residue was purified by preparative HPLC to give compound 4 (154 mg, yield: 44.25%).

$^1$H NMR (400 MHz, DMSO-$d_6$) δ 10.44-10.16 (m, 1H), 7.80-7.49 (m, 2H), 7.49-7.22 (m, 5H), 7.21-7.04 (m, 1H), 6.99-6.89 (m, 1H), 6.85-6.59 (m, 1H), 5.45-5.07 (m, 1H), 4.92-4.50 (m, 1H), 4.17-3.87 (m, 2H), 3.63-3.47 (m, 2H), 3.25-2.87 (m, 9H), 2.79-2.65 (m, 1H), 2.43-2.30 (m, 6H), 2.29-2.17 (m, 1H), 2.05-1.85 (m, 1H), 1.77-1.65 (m, 1H), 1.62-1.44 (m, 1H).

MS: m/z $[M+H]^+$: 614.2.

Example 4

Preparation of ((7-Chloro-1-(2-methyl-4-(2-methylbenzamido)benzoyl)-2,3,4,5-tetrahydro-1H-benzo[b]azepin-5-yl)oxy)methyl (2-(trimethylammonio)ethyl) phosphate (Compound 5)

5

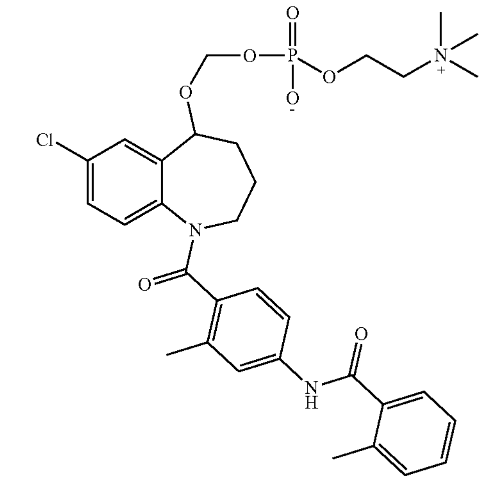

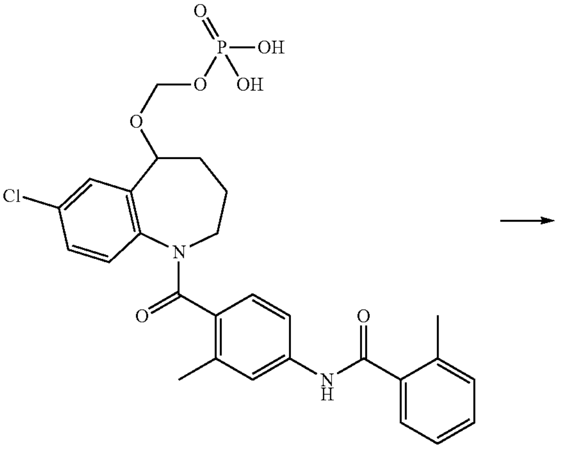

5-a

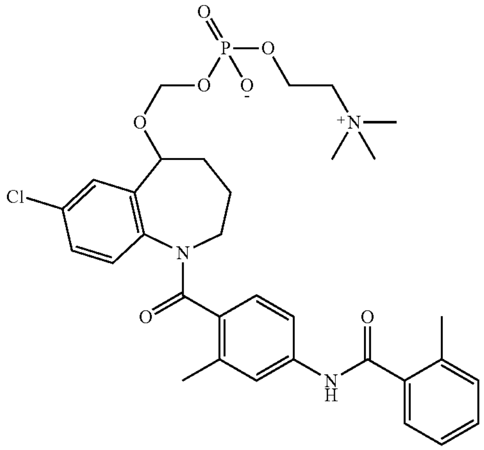

5

Compound 5-a (prepared according to the method disclosed in WO2009/1968) (368 mg, 0.660 mmol) was weighed into a reaction flask, and N,N-dimethylformamide (10 mL), potassium carbonate (910 mg, 6.60 mmol), and (2-bromoethyl)trimethylammonium bromide (1.63 g, 6.60 mmol) were added sequentially. The reaction was heated at 65° C. for 16 h. The reaction mixture was filtered. The filtrate was purified by preparative HPLC to give compound 5 (75 mg, yield: 17.68%).

$^{1}$H NMR (400 MHz, DMSO-$d_6$) δ 10.41-10.24 (m, 1H), 7.54-6.74 (m, 10H), 5.22-4.94 (m, 2H), 4.86-4.58 (m, 1H), 4.06-3.99 (m, 2H), 3.51-3.44 (m, 2H), 3.13-3.08 (m, 9H), 2.78-2.67 (m, 1H), 2.40-2.34 (m, 6H), 2.23-1.47 (m, 5H).

Example 5

Preparation of ((7-Chloro-1-(2-methyl-4-(2-methylbenzamido)benzoyl)-2,3,4,5-tetrahydro-1H-benzo[b]azepin-5-yl)oxy)methyl L-valinate (Compound 11) hydrochloride

11

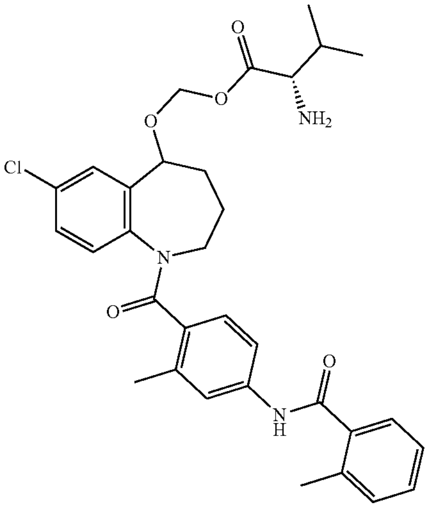

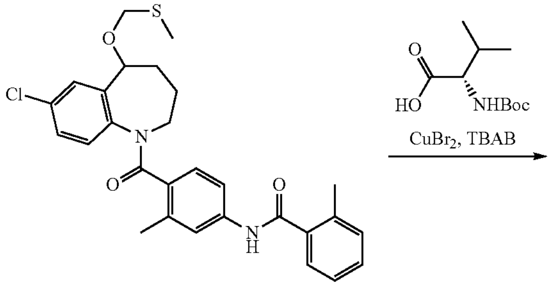

11-a

-continued

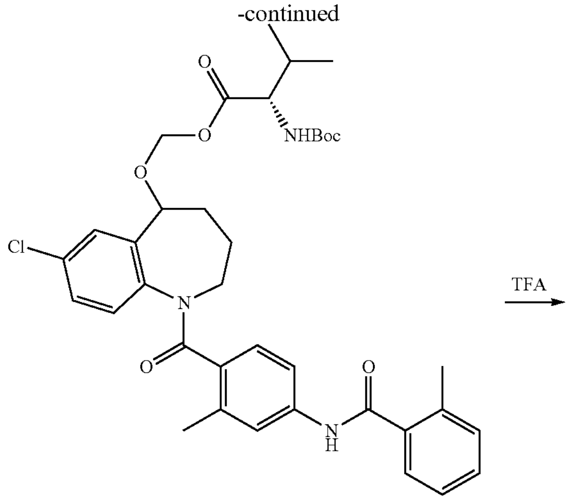

11-b

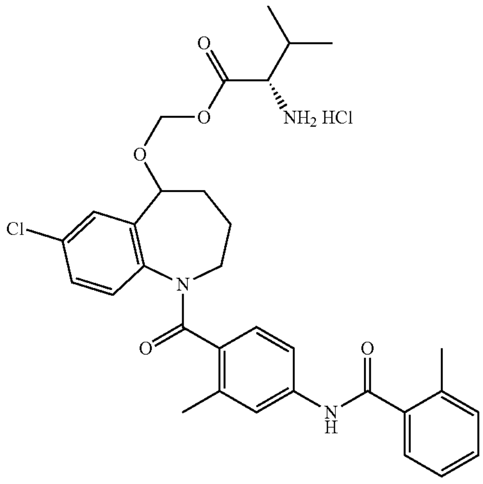

11

Step 1: Preparation of Compound 11-b

Compound 11-a (200 mg, 0.393 mmol) (prepared according to the method disclosed in US2011/71084), N-Boc-L-valine (85 mg, 0.393 mmol), copper bromide (263 mg, 1.18 mmol), TBAB (380 mg, 1.18 mmol) and molecular sieve (560 mg) were weighed out. The system was purged with nitrogen three times, and DMF (7.5 mL) was added under an ice-water bath. The mixture was stirred at room temperature for 10 min. The ice-water bath was removed, and the mixture was stirred at room temperature overnight. The reaction mixture was filtered through celite under reduced pressure, and the filter cake was washed with ethyl acetate (100 mL). The filtrate was washed with water (25 mL×3) and then saturated brine (25 mL). The organic phase was dried, filtered and concentrated under reduced pressure to give a crude product (650 mg). The crude product was separated and purified by silica gel column chromatography to give compound 11-b (270 mg, yield: 100%).

$^{1}$H NMR (400 MHz, $CDCl_3$) δ 8.07-6.45 (m, 10H), 5.68-5.31 (m, 2H), 5.20-4.65 (m, 3H), 4.32-4.12 (m, 1H), 2.60-2.35 (m, 6H), 2.28-2.11 (m, 1H), 1.86-1.60 (m, 4H), 1.52-1.19 (m, 9H), 1.05-0.77 (m, 6H).

Step 2: Preparation of Compound 11

Compound 11-b (270 mg, 0.398 mmol) was weighed out, and dichloromethane (24 mL) was added. The mixture was stirred to dissolve the compound completely. The solution was cooled to 5° C. in an ice-water bath in a nitrogen atmosphere, and TFA (3.0 mL) was added. After the addition, the mixture was stirred at that temperature for 2 h. The reaction mixture was concentrated under reduced pressure. The residue was purified by preparative HPLC to give compound 11 (77 mg, yield: 29%).

$^1$H NMR (400 MHz, DMSO-$d_6$) δ 10.44-10.17 (m, 1H), 8.38 (s, 3H), 7.82-7.19 (m, 8H), 7.19-6.91 (m, 1H), 6.87-6.61 (m, 1H), 5.83-5.43 (m, 2H), 5.38-5.06 (m, 1H), 5.01-4.80 (m, 1H), 4.58 (s, 1H), 4.02 (s, 1H), 2.44-2.28 (m, 6H), 2.26-2.07 (m, 2H), 2.07-1.87 (m, 1H), 1.85-1.66 (m, 1H), 1.65-1.43 (m, 1H), 1.10-0.70 (m, 6H).

Example 6

Preparation of ((((7-Chloro-1-(2-methyl-4-(2-methylbenzamido)benzoyl)-2,3,4,5-tetrahydro-1H-benzo[b]azepin-5-yl)oxy)formyloxy)methyl L-valinate (Compound 16) hydrochloride

16

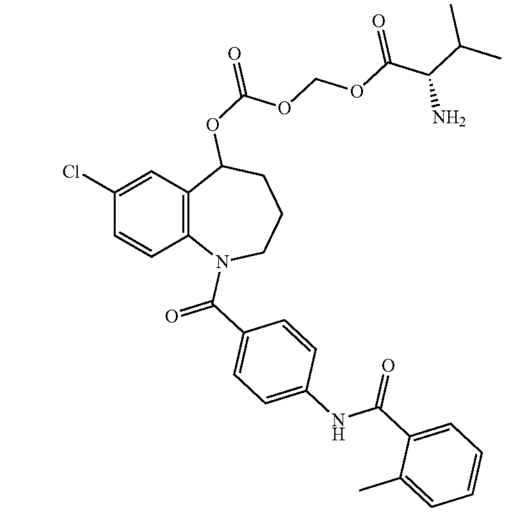

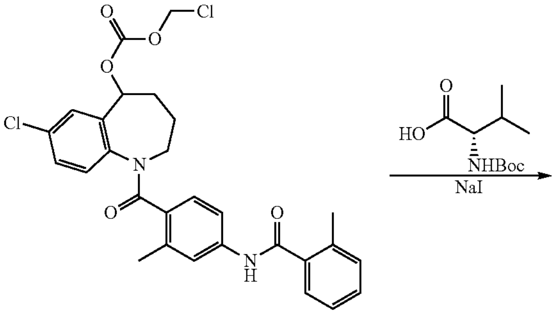

16-a

-continued

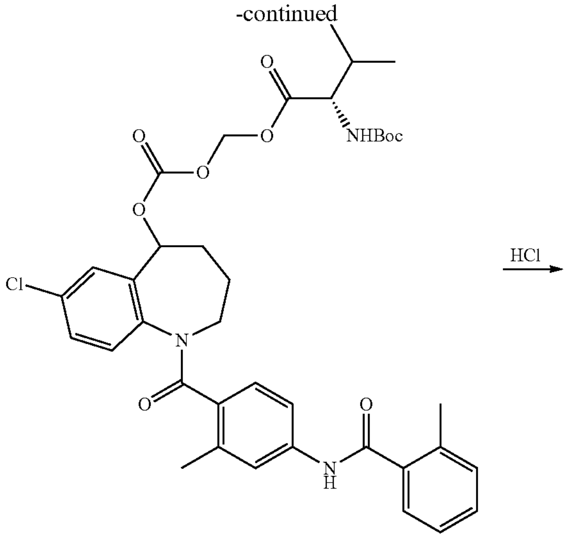

16-b

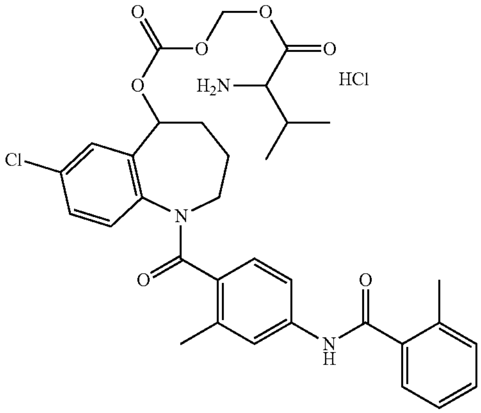

16

Step 1: Preparation of Compound 16-b

Compound 16-a (prepared according to the method disclosed in US2011/71084) (350 mg, 0.67 mmol) was weighed into a reaction flask, and N,N-dimethylformamide (4 mL) was added. The mixture was stirred at room temperature to dissolve the compound completely. After the system was purged with argon three times, sodium iodide (150 mg, 1.00 mmol), N-Boc-L-valine (220 mg, 1.50 mmol) and diisopropylethylamine (432 mg, 3.30 mmol) were added sequentially. The reaction was heated at 50-55° C. for 16 h. 20 mL of purified water was added to the reaction mixture, and the mixture was extracted with ethyl acetate (30 mL×2). The organic phase was collected, washed with a saturated aqueous solution of ammonium chloride, dried over anhydrous sodium sulfate, and concentrated under reduced pressure to give a crude compound 16-b (470 mg, yield: 97.01%).

MS: m/z [M+H]$^+$: 722.3.

Step 2: Preparation of (16)

Compound 16-b (470 mg, 0.650 mmol) was weighed into a reaction flask, and 1,4-dioxane (8 mL) was added. The mixture was cooled to 0-5° C., and a 4 mol/L solution of hydrogen chloride in dioxane (8 mL) was added. The mixture was stirred at room temperature for 1 h. The solvent was removed by concentration under reduced pressure. The crude product was purified by preparative HPLC to give the hydrochloride of compound 16 (175 mg, yield: 41.95%).

$^1H$ NMR (400 MHz, DMSO-$d_6$) δ 10.43-10.27 (m, 1H), 8.55 (s, 3H), 7.74-6.69 (m, 10H), 6.08-5.80 (m, 3H), 4.86-4.60 (m, 1H), 4.08-4.02 (m, 1H), 2.83-2.67 (m, 1H), 2.39-2.34 (m, 6H), 2.21-1.76 (m, 5H), 1.01-0.88 (m, 6H).

Example 7

Preparation of 2-(2-((7-Chloro-1-(2-methyl-4-(2-methylbenzamido)benzoyl)-2,3,4,5-tetrahydro-1H-benzo[b]azepin-5-yl)oxymethoxy)-2-oxoethoxy) acetic acid (Compound 14)

14

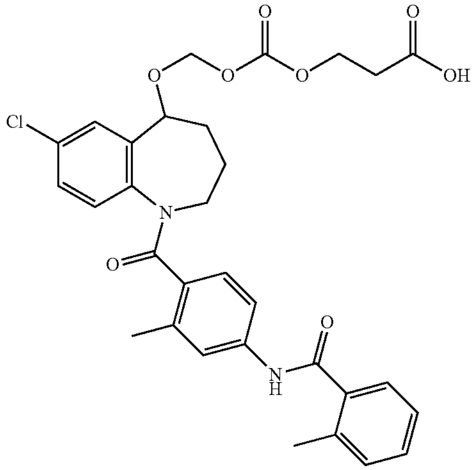

-continued

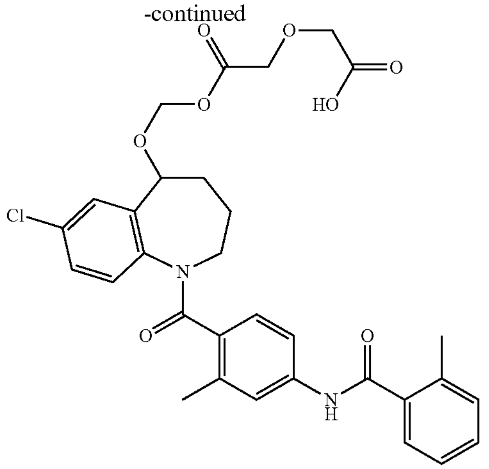

14

Compound 14-a (250 mg, 0.491 mmol) (prepared according to the method disclosed in US2011/71084), diglycolic acid (99 mg, 0.737 mmol), copper bromide (329 mg, 1.47 mmol), TBAB (475 mg, 1.47 mmol) and molecular sieve (700 mg) were weighed out. The system was purged with nitrogen three times. DMF (10 mL) was added under an ice-water bath, and the mixture was stirred at that temperature for 10 min. The ice-water bath was removed, and the mixture was stirred at room temperature for 2 h. The reaction mixture was filtered through celite under reduced pressure, and the filter cake was washed with ethyl acetate (100 mL). The filtrate was washed with water (40 mL×2) and then saturated brine (40 mL). The organic phase was dried, filtered and concentrated under reduced pressure to give a crude product (700 mg). The crude product was purified by preparative HPLC to give compound 14 (190 mg, yield: 65%). $^1H$ NMR (400 MHz, DMSO-$d_6$+$D_2O$) δ 7.77-6.61 (m, 10H), 5.60-4.45 (m, 4H), 4.20-3.95 (m, 2H), 3.92-3.78 (m, 3H), 2.41-2.28 (m, 6H), 2.25-1.35 (m, 4H).

Example 8

Preparation of Compound M

M

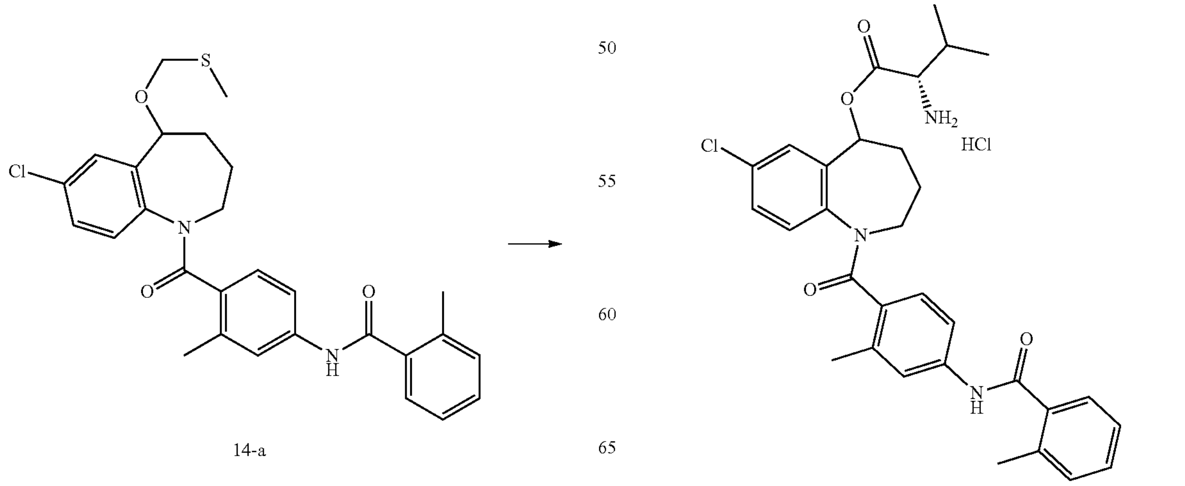

14-a

-continued

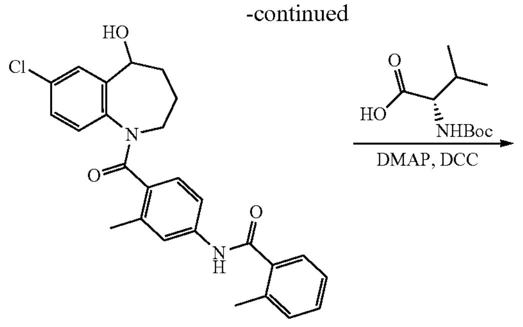

1-a

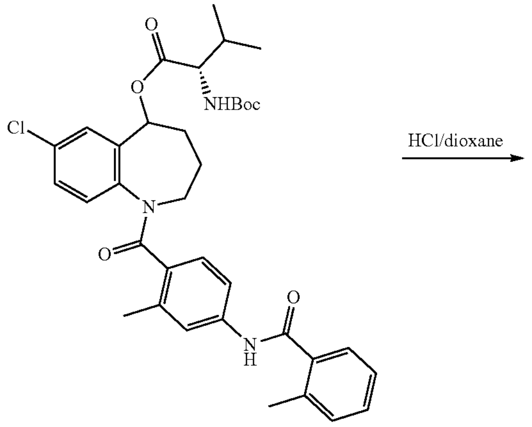

M-1

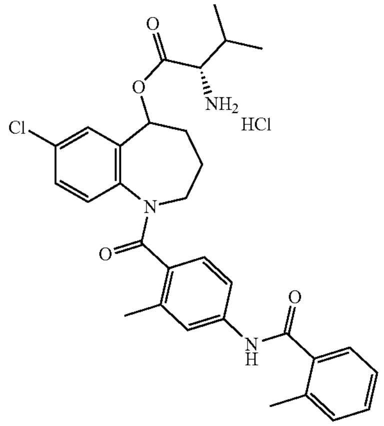

M

Step 1: Preparation of Compound M-1

Commercially available tolvaptan 1-a (500 mg, 1.11 mmol) was weighed out and dissolved in dichloromethane, N-(tert-butoxycarbonyl)-L-valine (291 mg, 1.34 mmol) and DMAP (13 mg, 0.11 mmol) were added, and DCC (276 mg, 1.34 mmol) was added under an ice bath. The reaction was conducted at room temperature overnight. The reaction mixture was filtered. The filtrate was concentrated under reduced pressure to give a pale yellow gum (890 mg, compound M-1). The gum was directly used in the next step without purification.

MS: calculated 647.3, found 648.3[M+H].

Step 2: Preparation of Compound M

Compound M-1 (1.11 mmol) was weighed out. The system was purged with nitrogen three times, and a solution of hydrogen chloride in dioxane (5.0 mL, 4.0 M) was added under an ice-water bath. The mixture was stirred at room temperature for 2 h. The reaction mixture was concentrated under reduced pressure to give a pale yellow solid (700 mg, crude). The crude product was separated and purified by reversed-phase column chromatography and lyophilized to give compound M as a white solid (450 mg, yield: 69%).

MS: calculated 547.2, found 548.2[M+H].

$^1$H NMR (400 MHz, $CDCl_3$) δ 8.99-8.41 (m, 3H), 8.11-5.87 (m, 11H), 4.88-0.396 (m, 1H), 2.81-0.87 (m, 20H).

Biological Assays

Test Example 1: Pharmacokinetic Study in Dogs

1. PK Study in Dogs 1.1. Study Protocol 1.1.1. Experimental Animals: Beagles, Non-Naïve, Sourced from the Animal Repository of Medicilon: 999M-004.

1.1.2. Administration Regimen:

| Group | Molecule | Number of animals (Male + female) | Route of administration | Dose (mg/kg) | Concentration (mg/mL) | Dose volume (mL/kg) |
|---|---|---|---|---|---|---|
| 1 | Tolvaptan | 2 + 1 | PO* | 1 | 0.5 | 2 |
| 2 | Compound 5 | 2 + 1 | PO* | 4.3 | 2.15 | 2 |

*All animals were fasted overnight (10-18 h) before administration and feeding was resumed 4 h after administration.

1.1.3. Sample Preparation Method

A proper amount of tolvaptan and compound 5 was accurately weighed out and well mixed with a proper volume of 1% hydroxypropyl methylcellulose by vortexing or ultrasonication to give a 0.5 mg/mL solution of tolvaptan and a 2.15 mg/mL solution of compound 5 for intragastric administration.

1.1.4. Test Method

Tolvaptan and compound 5 were intragastrically administrated. Blood was collected before the administration and 10 min, 30 min, 1 h, 2 h, 4 h, 6 h, 8 h and 24 h after the administration. EDTA-K2 was used as the anticoagulant, and the esterase inhibitor DDVP (manufacturer: Sigma) was added. Plasma samples were separated and cryopreserved at −70° C., and the compound 5 and tolvaptan levels were determined by LC-MS/MS.

1.2. Experimental Results

TABLE 1

| Molecule administrated | Molecule detected | | $T_{max}$ (h) | $C_{max}$ (ng/ml) | $AUC_{0-t}$ (h*ng/ml) | $AUC_{0-\infty}$ (h*ng/ml) | $t_{1/2}$ (h) |
|---|---|---|---|---|---|---|---|
| Tolvaptan | Tolvaptan | Mean value | 1.5 | 7.08 | 21.6 | 26.3 | 1.94 |
| | | SD | 0.866 | 1.66 | 6.76 | 5.28 | 0.527 |
| Compound 5 | Compound 5 | Mean value | 0.389 | 88.7 | 156 | 162 | 1.43 |
| | | SD | 0.193 | 5.8 | 36.9 | 33.7 | 0.8 |
| | Tolvaptan | Mean value | 2 | 45.9 | 347 | 372 | 4.22 |
| | | SD | 1.73 | 5.6 | 151 | 135 | 0.639 |

Note:
$T_{max}$ is the time to the peak concentration of the drug; $C_{max}$ is the peak concentration of the drug; $AUC_{0-t}$ and $AUC_{0-\infty}$ are areas under the drug concentration-time curve; $t_{1/2}$ is the half-life of the drug in the body.

After being intragastrically administered to beagles, compound 5 achieved a higher exposure and a longer half-life than tolvaptan after converting into tolvaptan in vivo.

Test Example 2: Inhibitory Activity of the Compound of the Present Invention Against Arginine Vasopressin Receptor 2 (AVPR2)

1. Arginine Vasopressin Receptor 2 (AVPR2) Receptor cAMP Assay 1.1. Sample Preparation Method The test compound was 5-fold diluted with assay buffer (Hank's balanced salt solution+20 mM HEPES+0.1% BSA+500 μM IBMX (manufacturer: Sigma)). The highest initial concentration of the test compound in the assay was 10 μM.

1.2. Cell Strain

Flpin-CHO-AVPR2 (the cell strain was constructed by Pharmaron Beijing Co., Ltd.; AVPR2 was derived from humans)

1.3. Test Method

1) Cells were digested, resuspended in assay buffer and inoculated into a 384-well cell culture plate at a density of 8000 cells per well and a volume of 15 μL per well.
2) The compound was diluted with assay buffer.
3) 2.5 μL of the compound was added to each well, and the plate was incubated at 37° C. for 10 min.
4) Arginine vasopressin (manufacturer: MedChemExpress) was diluted with assay buffer to a concentration of 16 μM.
5) 2.5 μL of the 16 μM solution of arginine vasopressin was added, and the plate was incubated at 37° C. for 30 min.
6) Eu-cAMP tracer and Ulight-anti-cAMP were thawed and diluted with lysis buffer (Eu-cAMP tracer, Ulight-anti-cAMP and lysis buffer were all taken from the cAMP assay kit (manufacturer: Perkin Elmer)).
7) 10 μL of Eu-cAMP tracer was added to the experimental wells, and then 10 μL of Ulight-anti-cAMP was added to the experimental wells.
8) The reaction plate was centrifuged at room temperature at 200 g for 30 s and left at 25° C. for 1 h, and data collection was performed using a microplate reader.

1.4. Experimental Results

TABLE 2

| Molecule | $IC_{50}$ (uM) |
|---|---|
| CN101346390 compound 1b disodium salt* | 0.047 |
| Compound 5 | 0.008 |

*Hereinafter referred to as compound 1b disodium salt

The results show that compound 5 has significantly higher inhibitory activity against the AVPR2 receptor than compound 1b disodium salt.

Test Example 3: Pharmacokinetic Study in Rats

1. PK Study in Rats 1.1. Study Protocol 1.1.1. Experimental Animals: SD Rats, Male and Female, Weighing about 220 g. Housing Environment: SPF. The Animals were Transferred from the Animal Repository (999M-017) of the Laboratory Animal Management Department, Shanghai Institute of Planned Parenthood Research.

1.1.2. Administration Regimen:

| Group | Molecule | Number of animals (Male + female) | Route of administration | Dose (mg/kg) | Concentration (mg/mL) | Dose volume (mL/kg) |
|---|---|---|---|---|---|---|
| 1 | Hydrochloride of compound 16 | 3 + 3 | i.v. | 4.41 | 0.882 | 5 |
| 2 | Compound M | 3 + 3 | i.v. | 3.91 | 0.782 | 5 |

1.1.3. Sample Preparation Method

A proper amount of the compound was accurately weighed out and well mixed with a proper volume of 10% DMSO+35% PEG400+55% normal saline by vortexing or ultrasonication to give a clear solution for intravenous injection.

1.1.4. Test Method

Blood was collected at various time points after intravenous injection (before the administration and 0.0833, 0.25, 0.5, 1, 2, 4, 8 and 24 h after the administration). EDTA-K2 was used as the anticoagulant, and the esterase inhibitor DDVP was added. Plasma samples were separated and cryopreserved at −70° C., and the compound and tolvaptan levels were determined by LC-MS/MS.

1.2. Experimental Results

TABLE 3

| Molecule administrated | Molecule detected | | $T_{max}$ (h) | $C_{max}$ (ng/ml) | $AUC_{0-t}$ (h*ng/ml) | $AUC_{0-\infty}$ (h*ng/ml) | $t_{1/2}$ (h) | Cl (ml/min/kg) | Vss (l/kg) |
|---|---|---|---|---|---|---|---|---|---|
| Hydrochloride of Compound 16 | Hydrochloride of Compound 16 | Undetectable | | | | | | | |
| | Tolvaptan | Mean value | 0.083 | 1180 | 1830 | 1860 | 1.02 | 57 | 3.45 |
| | | SD | 0 | 198 | 1110 | 1140 | 0.591 | 35.2 | 0.591 |
| Compound M | Compound M | Mean value | 0.139 | 719 | 786 | 824 | 1.17 | 90.8 | 6.47 |
| | | SD | 0.086 | 158 | 350 | 404 | 0.703 | 30 | 2.25 |
| | Tolvaptan | Mean value | 1.42 | 76.2 | 452 | 492 | 2.1 | — | — |
| | | SD | 0.665 | 41.3 | 514 | 516 | 0.941 | — | — |

Note:

"—" indicates it was not calculated.

The hydrochloride of compound 16 achieved a higher exposure than compound M after converting into tolvaptan in vivo, and converted faster than compound M.

Test Example 4: Pharmacokinetic Study in Rats

1. PK Study in Rats 1.1. Study Protocol 1.1.1. Experimental Animals: SD Rats, Male and Female, Weighing about 180-220 g. Housing Environment: SPF. The Animals were Transferred from the Animal Repository (999M-017) of the Laboratory Animal Management Department, Shanghai Institute of Planned Parenthood Research.

1.1.2. Administration Regimen:

| Group | Molecule | Number of animals (Male + female) | Route of administration | Dose (mg/kg) | Concentration (mg/mL) | Dose volume (mL/kg) |
|---|---|---|---|---|---|---|
| 1 | Tolvaptan | 3 + 3 | PO* | 9 | 0.9 | 10 |
| 2 | Compound 5 | 3 + 3 | PO* | 12.9 | 1.29 | 10 |

*All animals were fasted overnight (10-18 h) before administration and feeding was resumed 4 h after administration.

1.1.3. Sample Preparation Method

A proper amount of tolvaptan and compound 5 was accurately weighed out and well mixed with a proper volume of 1% hydroxypropyl methylcellulose by vortexing or ultrasonication to give a 0.9 mg/mL solution of tolvaptan and a 1.29 mg/mL solution of compound 5 for intragastric administration.

1.1.4. Test Method

Tolvaptan and compound 5 were intragastrically administrated. Blood was collected before the administration and 10 min, 0.5 h, 1 h, 2 h, 4 h, 6 h, 8 h and 24 h after the administration. EDTA-K2 was used as the anticoagulant, and the esterase inhibitor DDVP was added. Plasma samples were separated and cryopreserved at −70° C., and the compound 5 and tolvaptan levels were determined by LC-MS/MS.

1.2. Experimental results

TABLE 4

| Molecule adminis-trated | Molecule detected | Sex | | $T_{max}$ (h) | $C_{max}$ (ng/ml) | $AUC_{0-t}$ (h*ng/ml) | $t_{1/2}$ (h) |
|---|---|---|---|---|---|---|---|
| Tolvaptan | Tolvaptan | Female | Mean value | 2 | 412 | 1820 | 2.64 |
| | | | SD | 0 | 141 | 330 | 1.24 |
| | | Male | Mean value | 1.67 | 20.3 | 55.5 | N.A. |
| | | | SD | 0.577 | 5.55 | 19.8 | N.A. |
| Com-pound 5 | Com-pound 5 | Female | Mean value | 0.167 | 50.1 | 58.4 | 1.67 |
| | | | SD | 0 | 8.06 | 9.11 | 0.32 |
| | | Male | Mean value | 0.167 | 44.4 | 46.1 | 1.55 |
| | | | SD | 0 | 12.2 | 13.0 | 0.285 |
| | Tolvaptan | Female | Mean value | 5 | 319 | 2850 | 2.94 |
| | | | SD | 1 | 162 | 1120 | 0.356 |
| | | Male | Mean value | 3 | 32.3 | 165 | 3.44 |
| | | | SD | 1 | 9.99 | 22.7 | 1.74 |

The tolvaptan converted from compound 5 administered at an equivalent molar dose achieved a higher $AUC_{0-t}$ than tolvaptan.

Test Example 5: Pharmacokinetic Study in Beagles

1. PK Study in Beagles 1.1. Study Protocol 1.1.1. Experimental Animals: Beagles, Non-Naïve, Sourced from the Animal Repository of Medicilon: 999M-004.

1.1.2. Administration Regimen:

| Group | Molecule | Number of animals (Male) | Route of administration | Dose (mg/kg) | Concentration (mg/mL) | Dose volume (mL/Kg) |
|---|---|---|---|---|---|---|
| 1 | Normal saline | 3 | i.v. | — | — | 2 |
| 2 | Compound 1b disodium salt | 3 | i.v. | 1 | 0.5 | 2 |
| 3 | Compound 5 | 3 | i.v. | 0.5 | 0.25 | 2 |
| 4 | Compound 5 | 3 | i.v. | 2.7 | 1.35 | 2 |
| 5 | Tolvaptan | 3 | PO* | 10 | 5 | 2 |
| 6 | Compound 5 | 3 | PO* | 2.7 | 1.35 | 2 |

*All animals were fasted overnight (10-18 h) before administration and feeding was resumed 4 h after administration.

1.1.3. Sample Preparation Method

A proper amount of compound 1b disodium salt and compound 5 was accurately weighed out and well mixed with a proper volume of normal saline by vortexing or ultrasonication to give a 0.5 mg/mL clear solution of compound 1b disodium salt, a 0.25 mg/mL clear solution of compound 5 and a 1.35 mg/mL clear solution of compound 5 for intravenous drip administration.

A proper amount of tolvaptan and compound 5 was accurately weighed out and well mixed with a proper volume of 1% hydroxypropyl methylcellulose by vortexing or ultrasonication to give a 5 mg/mL solution of tolvaptan and a 1.35 mg/mL solution of compound 5 for intragastric administration.

1.1.4. Test Method

The compounds of the intravenous administration group were administered via an intravenous drip over 1 h. The compounds of the intragastric administration group were intragastrically administered. Time points of blood collection were: before the administration and 30 min, 1 h, 1.5 h, 2 h, 4 h, 6 h, 12 h and 24 h after the administration. About 1 mL of blood was collected via the jugular vein or in other suitable ways. EDTA-K2 was used as the anticoagulant, and the esterase inhibitor DDVP was added. Plasma samples were separated and cryopreserved at −70° C., and the levels of related compounds in vivo were determined by LC-MS/MS. About 0.5 mL of blood was collected via the jugular vein or in other suitable ways, placed into separator gel blood collection tubes (without an anticoagulant) and centrifuged at room temperature at 3500 rpm for 10 min to separate the serum, and the concentration of $Na^+$ in the serum was determined by using the ion-selective electrode method.

1.2. Experimental Results

TABLE 5

| Molecule adminis-trated | Molecule detected | | $T_{max}$ (h) | $C_{max}$ (ng/ml) | $AUC_{0-t}$ (h*ng/ml) | $t_{1/2}$ (h) |
|---|---|---|---|---|---|---|
| Compound 1b disodium salt 1 mg/kg i.v. | Compound 1b disodium salt | Mean value | 1 | 709 | 913 | 0.697 |
| | | SD | 0.5 | 244 | 584 | |
| | Tolvaptan | Mean value | 1.33 | 102 | 212 | 1.29 |
| | | SD | 0.577 | 17.8 | 52.4 | 0.392 |
| Compound 5 0.5 mg/kg i.v. | Compound 5 | Mean value | 1 | 889 | 1200 | 0.704 |
| | | SD | 0 | 76 | 86.6 | 0.0552 |
| | Tolvaptan | Mean value | 1.17 | 17.3 | 46.4 | 1.76 |
| | | SD | 0.289 | 2.07 | 5.42 | 0.232 |

TABLE 5-continued

| Molecule adminis-trated | Molecule detected | | $T_{max}$ (h) | $C_{max}$ (ng/ml) | $AUC_{0-t}$ (h*ng/ml) | $t_{1/2}$ (h) |
|---|---|---|---|---|---|---|
| Compound 5 2.7 mg/kg i.v. | Compound 5 | Mean value | 1 | 5700 | 7850 | 0.647 |
| | | SD | 0 | 236 | 149 | 0.0352 |
| | Tolvaptan | Mean value | 1 | 91.2 | 270 | 2.27 |
| | | SD | 0 | 22.1 | 30.2 | 0.224 |
| Tolvaptan 10 mg/kg p.o. | Tolvaptan | Mean value | 1.17 | 3.83 | 10.2 | 2.61 |
| | | SD | 0.289 | 1 | 2.3 | 1.28 |
| Compound 5 2.7 mg/kg p.o. | Compound 5 | Mean value | 0.5 | 61.5 | 122 | 1 |
| | | SD | 0 | 7.98 | 26.4 | 0.045 |
| | Tolvaptan | Mean value | 2 | 47.1 | 201 | 3.13 |
| | | SD | 0 | 11.7 | 40.7 | 1.21 |

FIG. 1 shows blood sodium curves of the compounds of the present invention in beagles. As shown in Table 5 and FIG. 1, the compound 5 administered via an intravenous drip at a lower dose than compound 1b disodium salt (0.5 mg/kg vs 1 mg/kg) can achieve a similar result in elevating the blood sodium level, which indicates that the compound 5 prototype molecule is active. The tolvaptan converted from the compound 5 administered intragastrically at a relatively low molar dose achieved a higher $AUC_{0-t}$ than the tolvaptan administered intragastrically, and has the effect of elevating the blood sodium level.

Test Example 6: Pharmacokinetic Study in Beagles

1. PK Study in Beagles
1.1. Study Protocol
1.1.1. Experimental Animals: Beagles (11±1.5 kg), Non-Naïve, Sourced from the Animal Repository of Sichuan Greentech.
1.1.2. Sample Preparation The tolvaptan tablets were commercially available (trade name: Ruibeitan (瑞贝坦); manufacturer: Jiangsu Hengrui Pharmaceuticals Co., Ltd.). The enteric-coated capsules of compound 5 were obtained by directly encapsulating a proper amount of compound 5 in enteric-coated capsules (manufacturer of the enteric-coated capsules: Qingdao Yiqing Biotech Co., Ltd.).

1.1.3. Administration regimen:

| Group | Drug | Route of administration | Dose | Frequency and period of administration |
|---|---|---|---|---|
| 1 | Tolvaptan tablets (containing 15 mg tolvaptan/tablet) | Oral administration | 2 tablets/animal | Single administration |
| 2 | Enteric-coated capsules of compound 5 (containing 20 mg of compound 5/capsule) | Oral administration | 2 capsules/animal | Single administration |

1.1.4. Test Method

Each group included 3 male beagles. Intact tolvaptan tablets (2 tablets/animal) and enteric-coated capsules of compound 5 (2 capsules/animal) were intragastrically administered. Blood was collected before the administration and 30 min, 1 h, 2 h, 4 h, 6 h, 8 h, 12 h and 24 h after the administration. EDTA-K2 was used as the anticoagulant, and the esterase inhibitor DDVP was added. Plasma samples were separated and cryopreserved at −70° C. The compound 5 and tolvaptan levels were determined by LC-MS/MS, and the urine volume during 0-6 h after the administration was recorded.

1.2. Experimental results

TABLE 6

| Administration | Molecule detected | | $T_{max}$ (h) | $C_{max}$ (ng/ml) | $AUC_{0-t}$ (h*ng/ml) | $t_{1/2}$ (h) |
|---|---|---|---|---|---|---|
| Tolvaptan tablets | Tolvaptan | Mean value | 1 | 98.5 | 359 | 3.6 |
| | | SD | 1.0-1.0 | 16.3 | 97.1 | 1.85 |
| Enteric-coated capsules of compound 5 | Compound 5 | Mean value | 2 | 39.9 | 84.5 | |
| | | SD | 0.5-4.0 | 2.86 | 21.1 | |
| | Tolvaptan | Mean value | 2 | 132 | 511 | 2.96 |
| | | SD | 2.0-4.0 | 50.5 | 98.6 | 1.26 |

Figure 2:
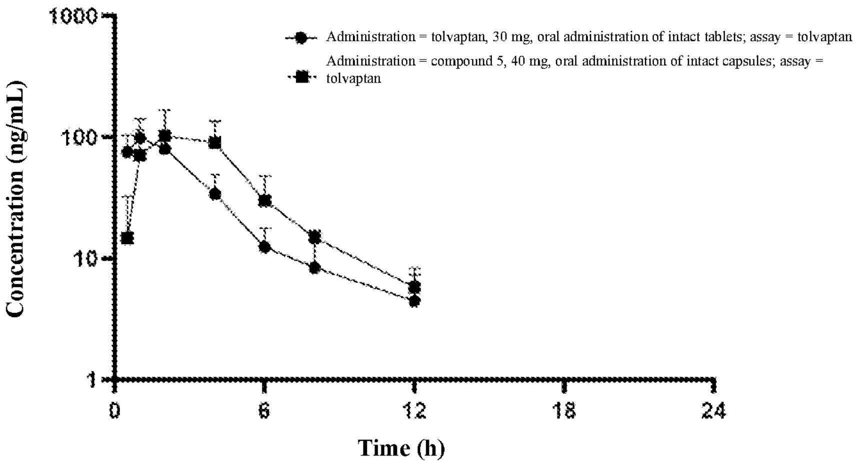
FIG. 2 shows PK curves in beagle plasma after oral administration of compound 5 capsules and tolvaptan tablets.
Figure 3:
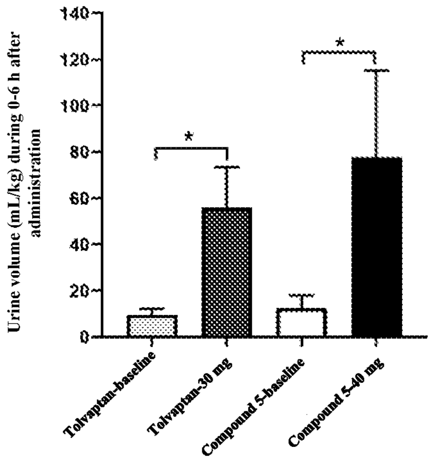
FIG. 3 shows the urine volume of beagles during 0-6 h after oral administration of compound 5 capsules and tolvaptan tablets.

FIG. 2 and FIG. 3 are the PK curves in beagle plasma and the urine volume during 0-6 h after oral administration of the enteric-coated capsules of compound 5 and tolvaptan tablets, respectively. As can be seen from Table 6 and FIG. 2, the tolvaptan converted in vivo from the enteric-coated capsules of compound 5 administered intragastrically to beagles at an equivalent molar dose achieved a higher $AUC_{0-t}$ than the tolvaptan tablets, and the effective concentration lasted about 2 more hours. As can be seen from FIG. 3, the intragastric administration of either the enteric-coated capsules of compound 5 or the tolvaptan tablets significantly increased the urine volume during 0-6 h after the administration to beagles.

The invention claimed is:

1. A compound of formula II-1 or a pharmaceutically acceptable salt thereof,

II-1

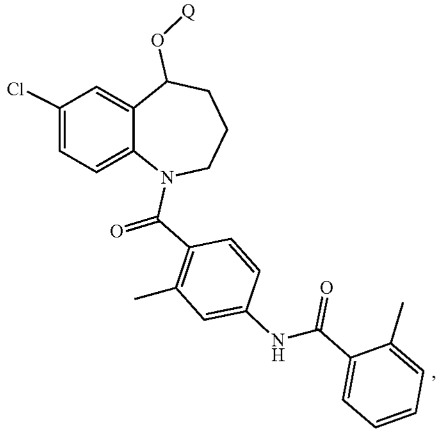

wherein,
Q is

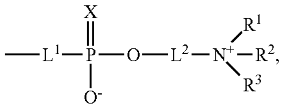

wherein:

$L^1$ is $-(CH_2)_m-$, and the $-(CH_2)-$ is optionally replaced by a heteroatom selected from the group consisting of O, S and N;

$L^2$ is $-(CH_2)_n-$, and the $-(CH_2)-$ is optionally replaced by a heteroatom selected from the group consisting of O, S and N;

m is selected from the group consisting of 0, 1, 2, 3, 4, 5 and 6;

n is selected from the group consisting of 1, 2, 3, 4, 5 and 6;

the $-(CH_2)-$ of $L^2$ is optionally substituted with A;

X is selected from the group consisting of O and S;

$R^1$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with group B;

$R^2$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with group B;

$R^3$ is selected from the group consisting of $C_{1-6}$ alkyl, $C_{3-8}$ cycloalkyl and 3-12 membered heterocyclyl; the $C_{1-6}$ alkyl, $C_{3-8}$ cycloalkyl and 3-12 membered heterocyclyl are optionally substituted with group B;

or $R^1$ and $R^2$ or $R^2$ and $R^3$, together with the N atom to which they are attached, form a 3-12 membered heterocyclyl group containing 1-3 heteroatoms; the 3-12 membered heterocyclyl group is optionally substituted with group B;

A is selected from the group consisting of H, —COOH, —$NH_2$, —OH, halogen, cyano, nitro, oxo, $C_{1-6}$ alkyl, $C_{1-6}$ alkoxy, $C_{3-8}$ cycloalkyl, 3-12 membered heterocyclyl, —$COR^4$, —$NHCOR^4$ and —$OCOR^4$; the —$NH_2$, $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —$NH_2$, —OH, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with one or more groups selected from the group consisting of —COOH, —$NH_2$, —OH, halogen, cyano, nitro, oxo, $C_{1-6}$ alkyl and $C_{1-6}$ alkoxy;

group B is selected from the group consisting of H, —COOH, —$NH_2$, —OH, halogen, cyano, nitro and oxo.

2. The compound of formula II-1 or the pharmaceutically acceptable salt thereof according to claim 1, wherein X is O.

3. The compound of formula II-1 or the pharmaceutically acceptable salt thereof according to claim 2, wherein n is selected from the group consisting of 2, 3, 4 and 5.

4. The compound of formula II-1 or the pharmaceutically acceptable salt thereof according to claim 2, wherein m is selected from the group consisting of 0, 1, 2, 3, 4 and 5.

5. The compound of formula II-1 or the pharmaceutically acceptable salt thereof according to claim 2, wherein A is selected from the group consisting of H, —COOH, —$NH_2$, —OH, halogen, cyano, nitro, oxo, $C_{1-6}$ alkyl, $C_{1-6}$ alkoxy, $C_{3-8}$ cycloalkyl and 3-12 membered heterocyclyl; the $C_{1-6}$ alkyl, $C_{1-6}$ alkoxy, $C_{3-8}$ cycloalkyl and 3-12 membered heterocyclyl are optionally substituted with $R^4$;

$R^4$ is selected from the group consisting of halogen, —$NH_2$, —OH and $C_{1-6}$ alkyl.

6. The compound of formula II-1 or the pharmaceutically acceptable salt thereof according to claim 5, wherein $L^1$ is —$CH_2$—O—, or $L^1$ is —$(CH_2)_m$—, and m is 0.

7. The compound of formula II-1 or the pharmaceutically acceptable salt thereof according to claim 6, wherein $L^2$ is —$(CH_2)_2$—.

8. The compound of formula II-1 or the pharmaceutically acceptable salt thereof according to claim 7, wherein $R^1$ is $C_{1-3}$ alkyl.

9. The compound of formula II-1 or the pharmaceutically acceptable salt thereof according to claim 8, wherein $R^2$ is $C_{1-3}$ alkyl.

10. The compound of formula II-1 or the pharmaceutically acceptable salt thereof according to claim 8, wherein $R^3$ is $C_{1-3}$ alkyl.

11. The compound of formula II-1 or the pharmaceutically acceptable salt thereof according to claim 1, wherein, X is O;

$L^1$ is —$(CH_2)_m$—, and m is 0; or $L^1$ is —$CH_2$—O—;

$L^2$ is —$(CH_2)_n$—, and n is selected from the group consisting of 2 and 3;

$R^1$ is selected from the group consisting of methyl, ethyl, n-propyl and isopropyl;

$R^2$ is selected from the group consisting of methyl, ethyl, n-propyl and isopropyl; and $R^3$ is selected from the group consisting of methyl, ethyl, n-propyl and isopropyl.

12. The compound of formula II-1 or the pharmaceutically acceptable salt thereof according to claim 11, wherein the compound is selected from the group consisting of:

4

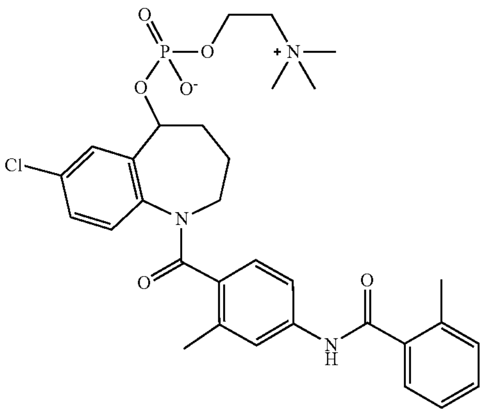

and

5

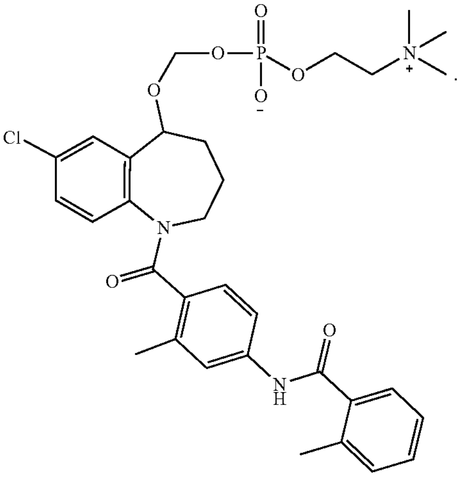

13. An isotopically substituted form of the compound or the pharmaceutically acceptable salt thereof according to claim 1, wherein the isotopic substitution is a substitution with a deuterium atom.

14. A pharmaceutical composition comprising at least one compound of formula II-1 or the pharmaceutically acceptable salt thereof according to claim 1, and a pharmaceutically acceptable excipient.

15. A method for treating hypertension, edema, abdominal dropsy, heart failure, renal dysfunction, syndrome of inappropriate vasopressin secretion, cirrhosis, hyponatremia, hypokalemia, diabetes, circulatory insufficiency, polycystic kidney disease, cerebral infarction or myocardial infarction in a subject in need thereof, the method comprising administering to the subject an effective amount of the pharmaceutical composition according to claim 14.

16. The compound of formula II-1 or the pharmaceutically acceptable salt thereof according to claim 3, wherein n is selected from the group consisting of 2 and 3.

17. The compound of formula II-1 or the pharmaceutically acceptable salt thereof according to claim 4, wherein m is selected from the group consisting of 0, 1, 2 and 3.

18. The compound of formula II-1 or the pharmaceutically acceptable salt thereof according to claim 5, wherein A is selected from the group consisting of H, —COOH, —$NH_2$, —OH, halogen, cyano and nitro.

19. The compound of formula II-1 or the pharmaceutically acceptable salt thereof according to claim 11, wherein, $R^1$ is methyl, $R^2$ is methyl, and $R^3$ is methyl.

* * * * *